US010774136B2

(12) United States Patent
Guo et al.

(10) Patent No.: US 10,774,136 B2
(45) **Date of Patent: *Sep. 15, 2020**

(54) ANTI-C5A BINDING MOIETIES WITH HIGH BLOCKING ACTIVITY

(71) Applicant: InflaRx GmbH, Jena (DE)

(72) Inventors: Renfeng Guo, Ann Arbor, MI (US); Niels Christoph Riedemann, Jena (DE); Yan Li, Beijing (CN); Beifen Shen, Beijing (CN)

(73) Assignee: INFLARX GMBH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/267,902

(22) Filed: Sep. 16, 2016

(65) Prior Publication Data

US 2017/0002067 A1 Jan. 5, 2017

Related U.S. Application Data

(63) Continuation of application No. 14/729,865, filed on Jun. 3, 2015, now Pat. No. 9,458,233, which is a continuation of application No. 14/317,968, filed on Jun. 27, 2014, now Pat. No. 9,073,983, which is a continuation of application No. 13/512,334, filed as application No. PCT/EP2010/007197 on Nov. 26, 2010, now Pat. No. 8,802,096.

(60) Provisional application No. 61/264,696, filed on Nov. 26, 2009.

(30) Foreign Application Priority Data

Nov. 26, 2009 (EP) .................................... 09014745

(51) Int. Cl.

| | |
|---|---|
| ***A61K 39/395*** | (2006.01) |
| ***C07K 16/28*** | (2006.01) |
| ***C07K 16/18*** | (2006.01) |
| ***C07K 14/00*** | (2006.01) |
| ***C07K 14/47*** | (2006.01) |
| *A61K 39/00* | (2006.01) |

(52) U.S. Cl.

CPC ............ *C07K 16/18* (2013.01); *A61K 39/395* (2013.01); *C07K 14/00* (2013.01); *C07K 14/47* (2013.01); *A61K 39/00* (2013.01); *C07K 2317/34* (2013.01); *C07K 2317/565* (2013.01); *C07K 2317/567* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 8,802,096 | B2 | 8/2014 | Guo et al. | |
| 9,073,983 | B2 | 7/2015 | Guo et al. | |
| 9,371,378 | B1 | 6/2016 | Rother et al. | |
| 9,458,233 | B2 * | 10/2016 | Guo | A61K 39/395 |
| 2004/0110226 | A1 * | 6/2004 | Lazar | C07K 16/00 435/7.1 |

FOREIGN PATENT DOCUMENTS

| | | |
|---|---|---|
| EP | 1 878 441 A2 | 1/2008 |
| JP | 2005-508889 | 4/2005 |
| WO | WO 01/15731 A1 | 3/2001 |
| WO | WO 03/015819 A1 | 2/2003 |

OTHER PUBLICATIONS

D'Angelo et al;, Many Routes to an Antibody Heavy-Chain CDR3: Necessary, Yet Insufficient, for Specific Binding, Frontiers in Immunology vol. 9, Article 395 Mar. 2018; doi:10.3389/fimmu.2018.00395. (Year: 2018).*

ABCAM Datasheet, "Anti-C5/C5a Antibody [557] (ab11876)," updated Jul. 26, 2012.

Ames, Robert S. et al. "Isolation of Neutralizing Anti-C5a Monoclonal Antibodies from a Filamentous Phage Monovalent Fab Display Library,"*Journal of Immunology*, 1994, 152:4572-4581.

Buras, Jon A. et al. "Animal Models of Sepsis: Setting the Stage," *Nature Reviews/Drug Discovery*, 2005, 4:854-865.

Chen, Ching et al. "Enhancement and destruction of antibody function by somatic mutation: unequal occurrence is controlled by V gene combinatorial associations,"*EMBO Journal*, 1995, 14(12):2784-2794.

Colman, P.M., "Effects of amino acid sequence changes on antibody-antigen interactions," *A Structural View of Immune Recognition by Antibodies*, 1994, 145:33-36.

Czermak, Boris J. et al., "Protective Effects of C5a Blockade in Sepsis," *Nature Medicine*, Jul. 1999, 5(7):788-792.

Ember, Julia A. et al. "Induction of Interleukin-8 Synthesis from Monocytes by Human C5a Anaphylatoxin," *American Journal of Pathology*, Feb. 1994, 144(2):393-403.

English translation of Office Action issued in corresponding Japanese Application No. 2012-540323, dated Jan. 8, 2015, wherein JP-2005-508889.

Fenglin, Lv et al., "The Interacted Kinetics Between B Cell Predominant Epitope Peptide of the Human C5a Anaphylatoxin and its Monoclonal Antibody," *Chinese Journal of Microbiology and Immunology*, 2003, 23(10):256-257.

(Continued)

*Primary Examiner* — Phillip Gambel

(74) *Attorney, Agent, or Firm* — Saliwanchik, Lloyd & Eisenschenk

(57) ABSTRACT

The present invention relates to binding moieties that specifically bind to a conformational epitope of C5a, in particular human C5a. Preferred binding moieties are anti-C5a antibodies that bind to this conformational epitope. The binding moieties described herein are useful as active agents in pharmaceutical compositions for the treatment and prevention of various acute and chronic diseases, in particular acute inflammatory diseases, such as the systemic inflammatory response syndrome (SIRS), and different degrees of sepsis including sepsis, severe sepsis, and septic shock.

10 Claims, 4 Drawing Sheets

Specification includes a Sequence Listing.

(56) References Cited

OTHER PUBLICATIONS

Johnson, Richard J. et al., "Identification of an Antigenic Epitope and Receptor Binding Domain of Human C5a" *The Journal of Immunology*, Jun. 1987, 138(11):3856-3862.
Klein, Christian et al., "Epitope interactions of monoclonal antibodies targeting CD20 and their relationship to functional properties," *mAbs*, 2013, 5(1):22-33.
Kola, Axel et al., "Epitope Mapping of a C5a Neutralizing mAb using a Combined Approach of Phage Display, Synthetic Peptides and Site-Directed Mutagenesis" *Immunotechnology*, 1996, 2:115-126.
Kussie, Paul H. et al., "A Single Engineered Amino Acid Substitution Changes Antibody Fine Specificity", *The American Association of Immunologists*, 1994, 152:146-152.
Larrick, James W. et al. "Characterization of Murine Monoclonal Antibodies that Recognize Neutralizing Epitopes on Human C5a" *Infection and Immunity*, Aug. 1987, 55(8):1867-1872.
Lederman, Seth et al. "A Single Amino Acid Substitution in a Common African Allele of the CD4 Molecule Ablates Binding of the Monoclonal Antibody, OKT4," *Molecular immunology*, 1991, 8:1171-1181.
Li, Choh Hao et al. "β-Endorphin omission analogs: Dissociation of immunoreactivity from other biological activities," *Proc. Natl. Acad. Sci. USA*, Jun. 1980, 77:3211-3214.
Manthey, Helga et al., "Complement component 5a (C5a)," The International Journal of Biochemistry & Cell Biology, 2009, 41:2114-2117.
Mollnes, Tom E. et al., "Strategies of Therapeutic Complement Inhibition," *Molecular Immunology*, 2006, 43:107-121.
Rittirsch, Daniel et al. "The Disconnect between Animal Models of Sepsis and Human Sepsis," *Journal of Leukocyte Biology*, 2007, 81:137-143.
Ruddikoff, Stuart et al. "Single amino acid substitution altering antigen-binding specificity," *Proc. Natl. Acad. Sci. USA*, Mar. 1982, 79:1979-1983.
Written Opinion of the International Searching Authority for corresponding PCT/EP2010/007197 (dated May 26, 2012).
Sela-Culang, Inbal, et al., "The structural basis of antibody-antigen recognition." Frontiers in Immunology, Oct. 2013, 4(302): 1-13.
Persson, H., et al., "CDR-H3 Diversity is Not Required for Antigen Recognition by Synthetic Antibodies." J Mol Biol., Feb. 2013, 425(4): 803-811.

* cited by examiner

SEQUENCE LISTING

```
<160> NUMBER OF SEQ ID NOS: 69

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70


<210> SEQ ID NO 2
<211> LENGTH: 9
<212> TYPE: PRT
<213> ORGANISM: Homo sapiens

<400> SEQUENCE: 2

Asn Asp Glu Thr Cys Glu Gln Arg Ala
1               5


<210> SEQ ID NO 3
<211> LENGTH: 7
<212> TYPE: PRT
<213> ORGANISM: Homo sapiens

<400> SEQUENCE: 3

Ser His Lys Asp Met Gln Leu
1               5


<210> SEQ ID NO 4
<211> LENGTH: 7
<212> TYPE: PRT
<213> ORGANISM: Homo sapiens

<400> SEQUENCE: 4

Asp Glu Thr Cys Glu Gln Arg
1               5


<210> SEQ ID NO 5
<211> LENGTH: 5
<212> TYPE: PRT
<213> ORGANISM: Homo sapiens

<400> SEQUENCE: 5

His Lys Asp Met Gln
1               5


<210> SEQ ID NO 6
<211> LENGTH: 13
<212> TYPE: PRT
<213> ORGANISM: Artificial Sequence
<220> FEATURE:
<223> OTHER INFORMATION: INab308 CDR3 heavy chain

<400> SEQUENCE: 6
```

-continued

Cys Ala Arg Gly Asn Asp Gly Tyr Tyr Gly Phe Ala Tyr
1 5 10

<210> SEQ ID NO 7
<211> LENGTH: 15
<212> TYPE: PRT
<213> ORGANISM: Artificial Sequence
<220> FEATURE:
<223> OTHER INFORMATION: INab708 CDR3 heavy chain

<400> SEQUENCE: 7

Cys Thr Arg Arg Gly Leu Tyr Asp Gly Ser Ser Tyr Phe Ala Tyr
1 5 10 15

<210> SEQ ID NO 8
<211> LENGTH: 10
<212> TYPE: PRT
<213> ORGANISM: Artificial Sequence
<220> FEATURE:
<223> OTHER INFORMATION: INab308 CDR3 light chain

<400> SEQUENCE: 8

Cys Gln Gln Ser Asn Glu Asp Pro Tyr Thr
1 5 10

<210> SEQ ID NO 9
<211> LENGTH: 10
<212> TYPE: PRT
<213> ORGANISM: Artificial Sequence
<220> FEATURE:
<223> OTHER INFORMATION: INab708 CDR3 light chain

<400> SEQUENCE: 9

Cys Gln Gln Asn Asn Glu Asp Pro Leu Thr
1 5 10

<210> SEQ ID NO 10
<211> LENGTH: 12
<212> TYPE: PRT
<213> ORGANISM: Artificial Sequence
<220> FEATURE:
<223> OTHER INFORMATION: INab308 CDR2 heavy chain

<400> SEQUENCE: 10

Ile Asp Pro Ser Asp Ser Glu Ser Arg Leu Asp Gln
1 5 10

<210> SEQ ID NO 11
<211> LENGTH: 12
<212> TYPE: PRT
<213> ORGANISM: Artificial Sequence
<220> FEATURE:
<223> OTHER INFORMATION: INab708 CDR2 heavy chain

<400> SEQUENCE: 11

Ile Leu Pro Gly Ser Gly Ser Thr Asn Tyr Asn Glu
1 5 10

<210> SEQ ID NO 12
<211> LENGTH: 7
<212> TYPE: PRT
<213> ORGANISM: Artificial Sequence
<220> FEATURE:
<223> OTHER INFORMATION: INab308 CDR2 light chain

<400> SEQUENCE: 12

Ile Tyr Ala Ala Ser Asn Leu 1 5

<210> SEQ ID NO 13
<211> LENGTH: 7
<212> TYPE: PRT
<213> ORGANISM: Artificial Sequence
<220> FEATURE:
<223> OTHER INFORMATION: INab708 CDR2 light chain

<400> SEQUENCE: 13

Ile Tyr Ala Ala Ser Asn Leu
1 5

<210> SEQ ID NO 14
<211> LENGTH: 14
<212> TYPE: PRT
<213> ORGANISM: Artificial Sequence
<220> FEATURE:
<223> OTHER INFORMATION: INab308 CDR1 heavy chain

<400> SEQUENCE: 14

Cys Lys Ala Ser Gly Tyr Ser Phe Thr Thr Phe Trp Met Asp
1 5 10

<210> SEQ ID NO 15
<211> LENGTH: 14
<212> TYPE: PRT
<213> ORGANISM: Artificial Sequence
<220> FEATURE:
<223> OTHER INFORMATION: INab708 CDR1 heavy chain

<400> SEQUENCE: 15

Cys Lys Ala Thr Gly Asn Thr Phe Ser Gly Tyr Trp Ile Glu
1 5 10

<210> SEQ ID NO 16
<211> LENGTH: 16
<212> TYPE: PRT
<213> ORGANISM: Artificial Sequence
<220> FEATURE:
<223> OTHER INFORMATION: INab308 CDR1 light chain

<400> SEQUENCE: 16

Cys Lys Ala Ser Gln Ser Val Asp Tyr Asp Gly Asp Ser Tyr Met Lys
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: INab708 CDR1 light chain

<400> SEQUENCE: 17

Cys Lys Ala Ser Gln Ser Val Asp Tyr Asp Gly Asp Ser Tyr Met Asn
1 5 10 15

<210> SEQ ID NO 18
<211> LENGTH: 9
<212> TYPE: PRT
<213> ORGANISM: Artificial Sequence
<220> FEATURE:
<223> OTHER INFORMATION: Consensus sequence of C5a in the region of amino acids 30-38
<220> FEATURE:
<221> NAME/KEY: VARIANT
<222> LOCATION: (1)..(1)
<223> OTHER INFORMATION: N, H, D, F, K, Y, or T

```
<220> FEATURE:
<221> NAME/KEY: VARIANT
<222> LOCATION: (2)..(2)
<223> OTHER INFORMATION: D, L, Y, or H
<220> FEATURE:
<221> NAME/KEY: VARIANT
<222> LOCATION: (6)..(6)
<223> OTHER INFORMATION: Q, E, or K
<220> FEATURE:
<221> NAME/KEY: VARIANT
<222> LOCATION: (8)..(8)
<223> OTHER INFORMATION: A, V, or L

<400> SEQUENCE: 18

Asn Asp Glu Thr Cys Glu Gln Arg Ala
1               5


<210> SEQ ID NO 19
<211> LENGTH: 7
<212> TYPE: PRT
<213> ORGANISM: Artificial Sequence
<220> FEATURE:
<223> OTHER INFORMATION: Consensus sequence of C5a in the region of
      amino acids 66-72
<220> FEATURE:
<221> NAME/KEY: VARIANT
<222> LOCATION: (1)..(1)
<223> OTHER INFORMATION: S, H, P, or N
<220> FEATURE:
<221> NAME/KEY: VARIANT
<222> LOCATION: (2)..(2)
<223> OTHER INFORMATION: H or N
<220> FEATURE:
<221> NAME/KEY: VARIANT
<222> LOCATION: (4)..(4)
<223> OTHER INFORMATION: D, N, H, P, or G
<220> FEATURE:
<221> NAME/KEY: VARIANT
<222> LOCATION: (5)..(5)
<223> OTHER INFORMATION: M, L, I, or V
<220> FEATURE:
<221> NAME/KEY: VARIANT
<222> LOCATION: (6)..(6)
<223> OTHER INFORMATION: Q, L, or I

<400> SEQUENCE: 19

Ser His Lys Asp Met Gln Leu
1               5


<210> SEQ ID NO 20
<211> LENGTH: 7
<212> TYPE: PRT
<213> ORGANISM: Artificial Sequence
<220> FEATURE:
<223> OTHER INFORMATION: Consensus sequence of C5a in the region of
      amino acids 31-37
<220> FEATURE:
<221> NAME/KEY: VARIANT
<222> LOCATION: (1)..(1)
<223> OTHER INFORMATION: D, L, Y, or H
<220> FEATURE:
<221> NAME/KEY: VARIANT
<222> LOCATION: (6)..(6)
<223> OTHER INFORMATION: Q, E, or K

<400> SEQUENCE: 20

Asp Glu Thr Cys Glu Gln Arg
1               5


<210> SEQ ID NO 21
<211> LENGTH: 5
<212> TYPE: PRT
<213> ORGANISM: Artificial Sequence
```

<220> FEATURE:
<223> OTHER INFORMATION: Consensus sequence of C5 in the region of amino
acids 67-71
<220> FEATURE:
<221> NAME/KEY: VARIANT
<222> LOCATION: (1)..(1)
<223> OTHER INFORMATION: H or N
<220> FEATURE:
<221> NAME/KEY: VARIANT
<222> LOCATION: (3)..(3)
<223> OTHER INFORMATION: D, N, H, P, or G
<220> FEATURE:
<221> NAME/KEY: VARIANT
<222> LOCATION: (4)..(4)
<223> OTHER INFORMATION: M, L, I, or V
<220> FEATURE:
<221> NAME/KEY: VARIANT
<222> LOCATION: (5)..(5)
<223> OTHER INFORMATION: Q, L, or I

<400> SEQUENCE: 21

His Lys Asp Met Gln
1 5

<210> SEQ ID NO 22
<211> LENGTH: 9
<212> TYPE: PRT
<213> ORGANISM: Macaca mulatta

<400> SEQUENCE: 22

His Asp Glu Thr Cys Glu Gln Arg Ala
1 5

<210> SEQ ID NO 23
<211> LENGTH: 7
<212> TYPE: PRT
<213> ORGANISM: Macaca mulatta

<400> SEQUENCE: 23

Ser His Lys Asp Leu Gln Leu
1 5

<210> SEQ ID NO 24
<211> LENGTH: 9
<212> TYPE: PRT
<213> ORGANISM: Sus scrofa

<400> SEQUENCE: 24

Asp Asp Glu Thr Cys Glu Glu Arg Ala
1 5

<210> SEQ ID NO 25
<211> LENGTH: 7
<212> TYPE: PRT
<213> ORGANISM: Sus scrofa

<400> SEQUENCE: 25

Ser His Lys Asn Ile Gln Leu
1 5

<210> SEQ ID NO 26
<211> LENGTH: 9
<212> TYPE: PRT
<213> ORGANISM: Equus caballus

<400> SEQUENCE: 26

Asp Leu Glu Thr Cys Glu Gln Arg Ala
1 5

<210> SEQ ID NO 27
<211> LENGTH: 7
<212> TYPE: PRT
<213> ORGANISM: Equus caballus

<400> SEQUENCE: 27

Ser His Lys His Ile Gln Leu
1               5

<210> SEQ ID NO 28
<211> LENGTH: 9
<212> TYPE: PRT
<213> ORGANISM: Bos taurus

<400> SEQUENCE: 28

Asp Asp Glu Thr Cys Glu Gln Arg Ala
1               5

<210> SEQ ID NO 29
<211> LENGTH: 7
<212> TYPE: PRT
<213> ORGANISM: Bos taurus

<400> SEQUENCE: 29

His His Lys Asn Met Gln Leu
1               5

<210> SEQ ID NO 30
<211> LENGTH: 9
<212> TYPE: PRT
<213> ORGANISM: Mus musculus

<400> SEQUENCE: 30

Phe Tyr Glu Thr Cys Glu Glu Arg Val
1               5

<210> SEQ ID NO 31
<211> LENGTH: 7
<212> TYPE: PRT
<213> ORGANISM: Mus musculus

<400> SEQUENCE: 31

Pro His Lys Pro Val Gln Leu
1               5

<210> SEQ ID NO 32
<211> LENGTH: 9
<212> TYPE: PRT
<213> ORGANISM: Rattus norvegicus

<400> SEQUENCE: 32

Lys Tyr Glu Thr Cys Glu Gln Arg Val
1               5

<210> SEQ ID NO 33
<211> LENGTH: 7
<212> TYPE: PRT
<213> ORGANISM: Rattus norvegicus

<400> SEQUENCE: 33

His His Lys Gly Met Leu Leu
1               5

<210> SEQ ID NO 34
<211> LENGTH: 9
<212> TYPE: PRT
<213> ORGANISM: Canis lupus

<400> SEQUENCE: 34

Tyr Asp Glu Thr Cys Glu Gln Arg Ala
1 5

<210> SEQ ID NO 35
<211> LENGTH: 7
<212> TYPE: PRT
<213> ORGANISM: Canis lupus

<400> SEQUENCE: 35

Ser Asn Lys Pro Leu Gln Leu
1 5

<210> SEQ ID NO 36
<211> LENGTH: 9
<212> TYPE: PRT
<213> ORGANISM: Monodelphis domestica

<400> SEQUENCE: 36

Thr His Glu Thr Cys Glu Lys Arg Leu
1 5

<210> SEQ ID NO 37
<211> LENGTH: 7
<212> TYPE: PRT
<213> ORGANISM: Monodelphis domestica

<400> SEQUENCE: 37

Asn His Lys Pro Val Ile Leu
1 5

<210> SEQ ID NO 38
<211> LENGTH: 7
<212> TYPE: PRT
<213> ORGANISM: Sus scrofa

<400> SEQUENCE: 38

Asp Glu Thr Cys Glu Glu Arg
1 5

<210> SEQ ID NO 39
<211> LENGTH: 7
<212> TYPE: PRT
<213> ORGANISM: Equus caballus

<400> SEQUENCE: 39

Leu Glu Thr Cys Glu Gln Arg
1 5

<210> SEQ ID NO 40
<211> LENGTH: 7
<212> TYPE: PRT
<213> ORGANISM: Mus musculus

<400> SEQUENCE: 40

Tyr Glu Thr Cys Glu Glu Arg
1 5

<210> SEQ ID NO 41
<211> LENGTH: 7

<212> TYPE: PRT
<213> ORGANISM: Rattus norvegicus

<400> SEQUENCE: 41

Tyr Glu Thr Cys Glu Gln Arg
1 5

<210> SEQ ID NO 42
<211> LENGTH: 7
<212> TYPE: PRT
<213> ORGANISM: Monodelphis domestica

<400> SEQUENCE: 42

His Glu Thr Cys Glu Lys Arg
1 5

<210> SEQ ID NO 43
<211> LENGTH: 5
<212> TYPE: PRT
<213> ORGANISM: Macaca mulatta

<400> SEQUENCE: 43

His Lys Asp Leu Gln
1 5

<210> SEQ ID NO 44
<211> LENGTH: 5
<212> TYPE: PRT
<213> ORGANISM: Sus scrofa

<400> SEQUENCE: 44

His Lys Asn Ile Gln
1 5

<210> SEQ ID NO 45
<211> LENGTH: 5
<212> TYPE: PRT
<213> ORGANISM: Equus caballus

<400> SEQUENCE: 45

His Lys His Ile Gln
1 5

<210> SEQ ID NO 46
<211> LENGTH: 5
<212> TYPE: PRT
<213> ORGANISM: Bos taurus

<400> SEQUENCE: 46

His Lys Asn Met Gln
1 5

<210> SEQ ID NO 47
<211> LENGTH: 5
<212> TYPE: PRT
<213> ORGANISM: Mus musculus

<400> SEQUENCE: 47

His Lys Pro Val Gln
1 5

<210> SEQ ID NO 48
<211> LENGTH: 5
<212> TYPE: PRT
<213> ORGANISM: Rattus norvegicus

<400> SEQUENCE: 48

His Lys Gly Met Leu
1 5

<210> SEQ ID NO 49
<211> LENGTH: 5
<212> TYPE: PRT
<213> ORGANISM: Canis lupus

<400> SEQUENCE: 49

Asn Lys Pro Leu Gln
1 5

<210> SEQ ID NO 50
<211> LENGTH: 5
<212> TYPE: PRT
<213> ORGANISM: Monodelphis domestica

<400> SEQUENCE: 50

His Lys Pro Val Ile
1 5

<210> SEQ ID NO 51
<211> LENGTH: 21
<212> TYPE: PRT
<213> ORGANISM: Artificial Sequence
<220> FEATURE:
<223> OTHER INFORMATION: INab308 FR1 heavy chain

<400> SEQUENCE: 51

Gln Val Gln Leu Gln Gln Ser Gly Pro Gln Leu Val Arg Pro Gly Thr
1 5 10 15

Ser Val Lys Ile Ser
20

<210> SEQ ID NO 52
<211> LENGTH: 15
<212> TYPE: PRT
<213> ORGANISM: Artificial Sequence
<220> FEATURE:
<223> OTHER INFORMATION: INab308 FR2 heavy chain

<400> SEQUENCE: 52

Trp Val Lys Gln Arg Pro Gly Gln Gly Leu Glu Trp Ile Gly Arg
1 5 10 15

<210> SEQ ID NO 53
<211> LENGTH: 33
<212> TYPE: PRT
<213> ORGANISM: Artificial Sequence
<220> FEATURE:
<223> OTHER INFORMATION: INab308 FR3 heavy chain

<400> SEQUENCE: 53

Arg Phe Lys Asp Arg Ala Thr Leu Thr Val Asp Lys Ser Ser Ser Thr
1 5 10 15

Val Tyr Met Gln Leu Ser Ser Pro Thr Ser Glu Asp Ser Ala Val Tyr
20 25 30

Tyr

<210> SEQ ID NO 54
<211> LENGTH: 12
<212> TYPE: PRT

<213> ORGANISM: Artificial Sequence
<220> FEATURE:
<223> OTHER INFORMATION: INab308 FR4 heavy chain

<400> SEQUENCE: 54

Trp Gly Gln Gly Thr Leu Val Thr Val Ser Ser Ala
1 5 10

<210> SEQ ID NO 55
<211> LENGTH: 22
<212> TYPE: PRT
<213> ORGANISM: Artificial Sequence
<220> FEATURE:
<223> OTHER INFORMATION: INab308 FR1 light chain

<400> SEQUENCE: 55

Asp Ile Val Leu Thr Gln Ser Pro Ala Ser Leu Ala Val Ser Leu Gly
1 5 10 15

Gln Arg Ala Thr Ile Ser
20

<210> SEQ ID NO 56
<211> LENGTH: 13
<212> TYPE: PRT
<213> ORGANISM: Artificial Sequence
<220> FEATURE:
<223> OTHER INFORMATION: INab308 FR2 light chain

<400> SEQUENCE: 56

Trp Tyr Gln Gln Lys Pro Gly Gln Pro Pro Lys Leu Leu
1 5 10

<210> SEQ ID NO 57
<211> LENGTH: 33
<212> TYPE: PRT
<213> ORGANISM: Artificial Sequence
<220> FEATURE:
<223> OTHER INFORMATION: INab308 FR3 light chain

<400> SEQUENCE: 57

Gln Ser Gly Ile Pro Ala Arg Phe Ser Gly Ser Gly Ser Gly Thr Asp
1 5 10 15

Phe Thr Leu Asn Ile His Pro Val Glu Glu Glu Asp Ala Ala Thr Tyr
20 25 30

Tyr

<210> SEQ ID NO 58
<211> LENGTH: 10
<212> TYPE: PRT
<213> ORGANISM: Artificial Sequence
<220> FEATURE:
<223> OTHER INFORMATION: INab308 FR4 light chain

<400> SEQUENCE: 58

Phe Gly Gly Gly Thr Lys Leu Glu Ile Lys
1 5 10

<210> SEQ ID NO 59
<211> LENGTH: 20
<212> TYPE: PRT
<213> ORGANISM: Artificial Sequence
<220> FEATURE:
<223> OTHER INFORMATION: INab708 FR1 heavy chain

<400> SEQUENCE: 59

Val Gln Leu Leu Glu Ser Gly Ala Glu Leu Met Lys Pro Gly Ala Ser
1 5 10 15

Val Lys Ile Ser
20

<210> SEQ ID NO 60
<211> LENGTH: 15
<212> TYPE: PRT
<213> ORGANISM: Artificial Sequence
<220> FEATURE:
<223> OTHER INFORMATION: INab708 FR2 heavy chain

<400> SEQUENCE: 60

Trp Val Lys Gln Arg Pro Gly His Gly Leu Glu Trp Ile Gly Glu
1 5 10 15

<210> SEQ ID NO 61
<211> LENGTH: 33
<212> TYPE: PRT
<213> ORGANISM: Artificial Sequence
<220> FEATURE:
<223> OTHER INFORMATION: INab708 FR3 heavy chain

<400> SEQUENCE: 61

Lys Phe Lys Gly Lys Ala Thr Leu Thr Ala Asp Thr Ser Ser Asn Thr
1 5 10 15

Ala Tyr Met Gln Leu Ser Ser Leu Thr Ser Glu Asp Ser Ala Val Tyr
20 25 30

Tyr

<210> SEQ ID NO 62
<211> LENGTH: 11
<212> TYPE: PRT
<213> ORGANISM: Artificial Sequence
<220> FEATURE:
<223> OTHER INFORMATION: INab708 FR4 heavy chain

<400> SEQUENCE: 62

Trp Gly Gln Gly Thr Leu Val Thr Val Ser Ala
1 5 10

<210> SEQ ID NO 63
<211> LENGTH: 22
<212> TYPE: PRT
<213> ORGANISM: Artificial Sequence
<220> FEATURE:
<223> OTHER INFORMATION: INab708 FR1 light chain

<400> SEQUENCE: 63

Asp Ile Val Leu Thr Gln Ser Pro Ala Ser Leu Ala Val Ser Leu Gly
1 5 10 15

Gln Arg Ala Thr Ile Ser
20

<210> SEQ ID NO 64
<211> LENGTH: 13
<212> TYPE: PRT
<213> ORGANISM: Artificial Sequence
<220> FEATURE:
<223> OTHER INFORMATION: INab708 FR2 light chain

<400> SEQUENCE: 64

Trp Tyr Gln Gln Lys Pro Gly Gln Pro Pro Lys Leu Leu
1 5 10

-continued

```
<210> SEQ ID NO 65
<211> LENGTH: 33
<212> TYPE: PRT
<213> ORGANISM: Artificial Sequence
<220> FEATURE:
<223> OTHER INFORMATION: INab708 FR3 light chain

<400> SEQUENCE: 65

Gly Ser Gly Ile Pro Ala Arg Phe Ser Gly Ser Gly Ser Gly Thr Asp
1               5                   10                  15

Phe Thr Leu Asn Ile His Pro Val Glu Glu Glu Val Ala Ala Thr Tyr
            20                  25                  30

Tyr


<210> SEQ ID NO 66
<211> LENGTH: 10
<212> TYPE: PRT
<213> ORGANISM: Artificial Sequence
<220> FEATURE:
<223> OTHER INFORMATION: INab708 FR4 light chain

<400> SEQUENCE: 66

Phe Gly Ala Gly Thr Leu Leu Glu Leu Lys
1               5                   10


<210> SEQ ID NO 67
<211> LENGTH: 13
<212> TYPE: PRT
<213> ORGANISM: Homo sapiens

<400> SEQUENCE: 67

Val Asn Asn Asp Glu Thr Cys Glu Gln Arg Ala Ala Arg
1               5                   10


<210> SEQ ID NO 68
<211> LENGTH: 6
<212> TYPE: PRT
<213> ORGANISM: Homo sapiens

<400> SEQUENCE: 68

Ile Ser His Lys Asp Met
1               5


<210> SEQ ID NO 69
<211> LENGTH: 5
<212> TYPE: PRT
<213> ORGANISM: Artificial Sequence
<220> FEATURE:
<223> OTHER INFORMATION: Peptide linker

<400> SEQUENCE: 69

Gly Gly Gly Gly Ser
1               5
```

ANTI-C5A BINDING MOIETIES WITH HIGH BLOCKING ACTIVITY

CROSS REFERENCE TO A RELATED APPLICATION

This Application is a Continuation Application of U.S. application Ser. No. 14/729,865, filed Jun. 3, 2015 (now U.S. Pat. No. 9,458,233); which is a Continuation Application of U.S. Ser. No. 14/317,968, filed Jun. 27, 2014, now U.S. Pat. No. 9,073,983; which is a Continuation Application of application Ser. No. 13/512,334, filed May 27, 2012, now U.S. Pat. No. 8,802,096; which is a National Stage Application of International Application Number PCT/EP2010/007197, filed Nov. 26, 2010; which claims priority to European Patent Application No. 09014745.5, filed Nov. 26, 2009; and claims the benefit of U.S. Provisional Application No. 61/264,696, filed Nov. 26, 2009; all of which are incorporated herein by reference in their entirety.

The Sequence Listing for this application is labeled "SeqList-27Jun14.txt", which was created on Jun. 27, 2014, and is 15 KB. The entire contents is incorporated herein by reference in its entirety.

FIELD OF THE INVENTION

The present invention relates to binding moieties that specifically bind to a conformational epitope of C5a, in particular human C5a. Preferred binding moieties are anti-C5a antibodies that bind to this conformational epitope. The binding moieties described herein are useful as active agents in pharmaceutical compositions for the treatment and prevention of various acute and chronic diseases, in particular acute inflammatory diseases, such as the systemic inflammatory response syndrome (SIRS), and different degrees of sepsis including sepsis, severe sepsis, and septic shock.

BACKGROUND OF THE INVENTION

C5a is cleaved from C5 upon complement activation. Among the complement activation products, C5a is one of the most potent inflammatory peptides, with a broad spectrum of functions (Guo and Ward 2005). C5a is a glycoprotein present in the blood of healthy humans with a molecular weight of 11.2 kDa. The polypeptide portion of C5a contains 74 amino acids, accounting for a molecular weight of 8.2 kDa while the carbohydrate portion accounts for approximately 3 kDa. C5a exerts its effects through the high-affinity C5a receptors (C5aR and C5L2) (Ward 2009). C5aR belongs to the rhodopsin-type family of G-protein-coupled receptors with seven transmembrane segments; C5L2 is similar but is not G-protein-coupled. It is currently believed that C5a exerts its biological functions primarily through C5a-C5aR interaction, as few biological responses have been found for C5a-C5L2 interaction. C5aR is widely expressed on myeloid cells including neutrophils, eosinophils, basophils, and monocytes, and nonmyeloid cells in many organs, especially in the lung and liver, indicative of the importance of C5a/C5aR signaling. C5a has a variety of biological functions (Guo and Ward 2005). C5a is a strong chemoattractant for neutrophils and also has chemotactic activity for monocytes and macrophages. C5a causes an oxidative burst ($O_2$ consumption) in neutrophils and enhances phagocytosis and release of granular enzymes. C5a has also been found to be a vasodilator. C5a has been shown to be involved in modulation of cytokine expression from various cell types, to enhance expression of adhesion molecules on neutrophils.

It is found that C5a becomes highly detrimental when it is overly produced in the disease settings, as it is a strong inducer and enhancer for inflammatory responses functioning in the up-stream of the inflammatory reaction chain. High doses of C5a can lead to nonspecific chemotactic "desensitization" for neutrophils, thereby causing broad dysfunction (Huber-Lang et al. 2001a).

C5a has been reported to exert numerous pro-inflammatory responses, and has been reported to be harmful during sepsis. Inhibition of C5a or of the C5a receptor (C5aR) by antibodies has been demonstrated to dramatically improve survival in various sepsis models in mice and rats (Czermak et al. 1999; Guo et al. 2000; Huber-Lang et al. 2001b; Riedemann et al. 2002a). In addition, various reports have demonstrated harmful effects of C5a for intact innate immune- and organ functions during experimental sepsis (Guo et al. 2000; Guo et al. 2002; Huber-Lang et al. 2001a; Huber-Lang et al. 2002; Laudes et al. 2002; Riedemann et al. 2003; Riedemann et al. 2004a; Riedemann et al. 2004b). C5a acts as an anaphylatoxin and has been reported to exert numerous pro-inflammatory effects. In human, sepsis high levels of C5a have been reported to be associated with significantly worsened outcome in various studies (Bengtson and Heideman 1988; Nakae et al. 1994; Nakae et al. 1996).

In the experimental setting of sepsis, exposure of neutrophils to C5a can lead to neutrophil dysfunction and paralysis of signaling pathways, leading to defective assembly of NADPH oxidase, paralysis of MAPK signaling cascades, a greatly depressed oxidative burst, phagocytosis and chemotaxis (Guo et al. 2006a; Huber-Lang et al. 2002). Thymocyte apoptosis and delayed neutrophil apoptosis are two important pathogenic events for sepsis development, which are dependent on the presence of C5a (Guo et al. 2000; Guo et al. 2006b). During experimental sepsis, C5a up-regulates β2 integrin expression on neutrophils to promote cell migration into organs (Guo et al. 2002), one of the major causes for multiorgan failure (MOF). It is also found that C5a is attributable to the activation of the coagulation pathway that occurs in the experimental sepsis (Laudes et al. 2002). C5a stimulates the synthesis and release from human leukocytes of pro-inflammatory cytokines such as TNF-α, IL-β, IL-6, IL-8, and macrophage migration inhibitory factor (MIF) (Hopken et al. 1996; Riedemann et al. 2004a; Strieter et al. 1992). C5a produces a strong synergistic effect with LPS in production of TNF-α, macrophage inflammatory protein (MIP)-2, cytokine-induced neutrophil chemoattractant (CINC)-1, and IL-1β in alveolar epithelial cells (Riedemann et al. 2002b; Rittirsch et al. 2008). Given that complement activation is an event occurring during the onset of sepsis, C5a may come into play before emergence of the "inflammatory cytokine storm". It appears that C5a plays a key role in orchestrating the performance of the cytokine network and the formation of systemic inflammatory response syndrome (SIRS). Blockade of C5a in the setting of experimental sepsis dramatically attenuates MOF and SIRS. Widespread up-regulation of C5aR expression occurs during onset of sepsis, and blockade of C5a/C5aR interaction by anti-C5a, or anti-C5aR antibodies, or C5aR antagonists renders highly protective effects in rodent models of sepsis (Czermak et al. 1999; Huber-Lang et al. 2001b; Riedemann et al. 2002a).

In addition to the sepsis indication, blockade of C5a has also been proven to be protective in many other models of inflammation such as ischemia/reperfusion injury, renal disease, graft rejection, malaria, rheumatoid arthritis, infectious bowel disease, inflammatory lung disease, lupus-like auto-immune diseases, neurodegenerative disease, etc. in various species as partially reviewed under Klos A. et al (Klos et al. 2009) and Allegretti M. et al (Allegretti et al. 2005). Moreover, it has been recently discovered that blockade of C5a has shown a strong therapeutic benefit in a tumor model in mice (Markiewski et al, 2008).

Technical Problems Underlying the Present Invention

Antibodies that specifically bind to the C5a part but not to the C5b part of C5 are known from the prior art (Klos et al. (1998) J. Immunol. Meth. 111: 241-252; WO 01/15731; WO 03/015819).

However, previously generated anti-C5a antibodies exhibited only moderate blocking activities on biological effects induced by C5a. In consequence, anti-C5a antibodies of the prior art were either not capable of achieving a complete blockade of C5a-induced biological effects or had to be used in superstoichiometric amounts to reach a reasonably high blockage of C5a activity.

Thus, especially in view of a potential clinical use in patients, there remained a need in the prior art for anti-C5a antibodies or other binding moieties displaying a stronger blocking activity for C5a-induced biological effects while specifically binding to C5a with high affinity. Also, preferably such antibodies should not bind to C5b and consequently should not affect the biological activities of C5b.

Quite surprisingly, the inventors of the present invention were able to identify a new conformational binding epitope with corresponding binding antibodies that fulfil the above mentioned advanced requirements and others. In tedious experiments underlying the present invention, two anti-C5a antibodies out more than 2000 could be generated that exhibit an unprecedented blocking activity to C5a-induced biological effects when employed in stoichiometric amounts, i.e. 0.5 mole of a bivalent antibody per mole of C5a.

The above overview does not necessarily describe all problems solved by the present invention.

SUMMARY OF THE INVENTION

In a first aspect the present invention relates to a binding moiety which binds to a conformational epitope formed by amino acid sequences $X_1X_2ETCEX_3RX_4$ (SEQ ID NO: 18) and $X_5X_6KX_7X_8X_9L$ (SEQ ID NO: 19) of C5a, wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I.

In a second aspect the present invention relates to an antibody or an antigen-binding fragment thereof comprising: (i) a heavy chain CDR3 sequence as set forth in SEQ ID NO: 6; or (ii) a heavy chain CDR3 sequence as set forth in SEQ ID NO: 7; wherein the heavy chain CDR3 sequence optionally comprises 1, 2 or 3 amino acid exchanges, 1, 2, or 3 amino acid deletions and/or 1, 2, or 3 amino acid additions.

In a third aspect the present invention relates to a pharmaceutical composition comprising (a) the binding moiety according to the first aspect or (b) the antibody or antigen-binding fragment thereof according to the second aspect and further comprising one or more pharmaceutically acceptable carriers, diluents, excipients, fillers, binders, lubricants, glidants, disintegrants, adsorbents, and/or preservatives.

In a fourth aspect the present invention relates to a use of (a) a binding moiety according to the first aspect or (b) an antibody or antigen-binding fragment thereof according to the second aspect for the preparation of a pharmaceutical composition for the prevention and or treatment of various diseases involving acute inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving a chronic type of inflammation such as renal glomerular diseases such as glomerulonephritis and other entities of renal failure, rheumatoid arthritis and similar auto-immune diseases such as Bechterew's disease, lupus-type diseases, inflammatory bowel disease, Crohn's disease, tumor growth, or solid organ cancer.

In a fifth aspect the present invention is directed to a method of treating systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, renal glomerular diseases such as glomerulonephritis and other entities of renal failure, rheumatoid arthritis and similar auto-immune diseases such as Bechterew's disease, lupus-type diseases, inflammatory bowel disease, Crohn's disease, tumor growth, or solid organ cancer in a patient in need thereof, the method comprising administering to the patient an effective amount of (a) a binding moiety according to the first aspect or (b) an antibody or antigen-binding fragment thereof according to the second aspect.

This summary of the invention does not necessarily describe all features of the invention.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

As used herein, "human C5a" refers to the following 74 amino acid peptide:

```
                                        (SEQ ID NO: 1)
TLQKKIEEIA AKYKHSVVKK CCYDGACVNN DETCEQRAAR

ISLGPRCIKA FTECCVVASQ LRANISHKDM QLGR.
```

The term "binding moiety", as used herein, refers to any molecule or part of a molecule that can specifically bind to a target molecule or target epitope. Preferred binding moieties in the context of the present application are (a) antibodies or antigen-binding fragments thereof; (b) oligonucleotides; (c) antibody-like proteins; or (d) peptidomimetics. "Binding moieties" that can be used for practicing the present invention are capable of binding to a conformational epitope of mammalian C5a which is formed by the two amino acid sequences $X_1X_2ETCEX_3RX_4$ (SEQ ID NO: 18) and $X_5X_6KX_7X_8X_9L$ (SEQ ID NO: 19), wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I. "Binding moieties" that are particularly suitable for practicing the present invention are capable of binding to a conformational epitope of human C5a which is formed by the two amino acid sequences NDETCEQRA (SEQ ID NO: 2) and SHKDMQL (SEQ ID NO: 3).

As used herein, a first compound (e.g. an antibody) is considered to "bind" to a second compound (e.g. an antigen, such as a target protein), if it has a dissociation constant $K_d$ to said second compound of 1 mM or less, preferably 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant ($K_d$) which is lower than the dissociation constant for the second target. Preferably the dissociation constant ($K_d$) for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding moiety does not bind specifically.

As used herein, the term "$K_d$" (measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof).

An "epitope", also known as antigenic determinant, is the part of a macromolecule that is recognized by the immune system, specifically by antibodies, B cells, or T cells. As used herein, an "epitope" is the part of a macromolecule capable of binding to a binding moiety (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which a binding moiety of the invention (e.g. an antibody or an antigen-binding fragment thereof) binds simultaneously, wherein these at least two separate regions are interrupted by one more regions in the primary sequence to which a binding moiety of the invention does not bind. Preferably, such a "conformational epitope" is present on a polypeptide, and the two separate regions in the primary sequence are two separate amino acid sequences to which a binding moiety of the invention (e.g. an antibody or an antigen-binding fragment thereof) binds, wherein these at least two separate amino acid sequences are interrupted by one more amino acid sequences in the primary sequence to which a binding moiety of the invention does not bind. Preferably, the interrupting amino acid sequence is a contiguous amino acid sequence comprising two or more amino acids to which the binding moiety does not bind. The at least two separate amino acid sequences to which a binding moiety of the invention binds are not particularly limited with regard to their length. Such a separate amino acid sequence may consists of only one amino acid as long as the total number of amino acids within said at least two separate amino acid sequences is sufficiently large to effect specific binding between the binding moiety and the conformational epitope.

A "paratope" is the part of an antibody that recognizes the epitope. In the context of the present invention, a "paratope"

is the part of a binding moiety (e.g. an antibody or antigen-binding fragment thereof) as described herein that recognizes the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1. Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007.

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope, e.g. to the conformational epitope of C5a formed by the amino acid sequences $X_1X_2ETCEX_3RX_4$ (SEQ ID NO: 18) and $X_5X_6KX_7X_8X_9L$ (SEQ ID NO: 19), wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I; or to the conformational epitope of human C5a formed by the amino acid sequences according to SEQ ID NO: 2 and SEQ ID NO: 3; or the conformational epitope of human C5a formed by the amino acid sequences DETCEQR (SEQ ID NO: 4) and KDM. The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgA1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, the content of which is herein incorporated by reference in its entirety. The review article by Almagro & Fransson is briefly summarized in the following. Almagro & Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

CDR Grafting

A CDR grafting protocol typically comprises three decision-making points: (1) definition of regions determining the specificity of the donor antibody, i.e. the target for grafting, (2) identification of a source of human sequences to be utilized as FR donors, and (3) selection of residues outside of the region defining the specificity, i.e. determining amino acid positions that are targets for back mutation to restore or improve the affinity of the humanized antibody.

(1) Regions Determining the Antibody Specificity

The experimental structure of the non-human antibody in complex with the antigen provides a detailed map of residues in contact with the antigen and therefore those responsible for determining its specificity. The structural information can be complemented with alanine scanning mutagenesis and/or combinatorial mutagenesis to identify the residues contributing most to the binding energy or to the functional paratope. Since the functional paratope is a subset of the residues in contact, grafting only the functional paratope would reduce the number of non-human residues in the humanized product. However, only in rare cases are the experimental structure of the antigen-antibody complex and/or the functional paratope available at the beginning of a humanization protocol. In absence of a precise definition of residues responsible for a given antibody specificity, CDRs are often employed as regions defining the specificity. It is also possible to use a combination of CDR and HV loop as targets for grafting. To reduce the number of residues to be grafted on the human FRs, SDR grafting has been described, i.e. the grafting of specificity-determining residues (SDRs).

(2) Source of Human FRs

The second step in a typical CDR grafting protocol is to identify human FR donors. Initial works utilized FRs of human antibodies of known structure, regardless of their homology to the non-human antibody. This approach is known as "Fixed FR method". Later works used human sequences having the highest homology to the non-human antibody. This approach has been termed "Best Fit". While "best fit" strategies tend to result in antibodies with higher affinity, other parameters such as low immunogenicity and production yields have to be taken into account, too, when choosing an FR for humanization. Thus, combinations of "best fit" and "fixed FR" are also possible. For example, the $V_L$ part can be humanized according to the fixed FR method and the $V_H$ part can be humanized according to the best fit method, or vice versa.

Two sources of human sequences have been utilized: mature and germline sequences. Mature sequences, which are products of immune responses, carry somatic mutations generated by random processes and are not under the species selection, resulting in potential immunogenic residues. Thus, to avoid immunogenic residues, human germline genes have increasingly been utilized as source of FR donors. Nucleotide sequences of human germline FRs are disclosed e.g. in Appendices A and B of the article by Dall'Acqua et al, 2005. Furthermore, germline gene based antibodies tend to be more flexible as compared to mature antibodies. This higher flexibility is thought to better accommodate diverse CDRs with fewer or no back mutations into the FR to restore the affinity of the humanized antibody.

(3) Back Mutations to Restore or Enhance Affinity

Commonly, affinity decreases after CDR grafting as a consequence of incompatibilities between non-human CDRs and human FRs. Therefore, the third step in a typical CDR grafting protocol is to define mutations that would restore or prevent affinity losses. Back mutations have to be carefully designed based on the structure or a model of the humanized antibody and tested experimentally.

Resurfacing

Resurfacing is similar to CDR grafting and shares the first two decision-making points. In contrast to CDR grafting, resurfacing retains the non-exposed residues of the non-human antibody. Only surface residues in the non-human antibody are changed to human residues.

Superhumanization

While CDR grafting relies on the FR comparison between the non-human and the humans sequences, superhumanization is based on a CDR comparison so that FR homology is irrelevant. The approach includes a comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs.

Human String Content Optimization

This approach is based on a metric of antibody "humanness", termed Human String Content (HSC). In short, this approach compares the mouse sequence with the repertoire of human germline genes. Differences are scored as HSC. The target sequence is the humanized by maximizing its HSC rather than using a global identity measure to generate multiple diverse humanized variants.

Framework Libraries (Abbreviated: FR Libraries)

In the FR library approach, a collection of residue variants are introduced at specific positions in the FR followed by panning of the library to select the FR that best supports the grafted CDR. Thus, this approach resembles CDR grafting but instead of creating a few back mutations in the FR, a combinatorial library of typically more than 100 mutational variants is constructed.

Guided Selection

This approach includes combining the $V_H$ or $V_L$ domain of a given non-human antibody specific for a particular antigen with a human $V_H$ and $V_L$ library. Subsequently, specific human V domains are selected against the antigen of interest. For example, a non-human antibody can be humanized by first combining the non-human $V_H$ with a library of human light chains. The library is then selected against the target antigen by phage display and the selected $V_L$ is cloned into a library of human $V_H$ chains and selected against the target antigen. It is also possible to start with combining the non-human $V_L$ with a library of human heavy chains. The library is then selected against the target antigen by phage display and the selected $V_H$ is cloned into a library of human $V_L$ chains and selected against the target antigen. As a result, a fully human antibody with similar affinity as the non-human antibody can be isolated. To avoid the occurrence of an epitope drift, it is possible to implement a so-called inhibition ELISA, which allows for the selection of clones recognizing the same epitope as the parent antibody. Alternatively, CDR retention can be applied to avoid an epitope drift. In CDR retention, one or more non-human CDRs are retained, preferably the heavy chain CDR3, since this CDR is at the center of the antigen binding site.

Framework Shuffling (Abbreviated: FR Shuffling)

In the FR shuffling approach, whole FRs are combined with the non-human CDRs. Using FR shuffling, Dall'Acqua and co-workers humanized a murine antibody. All six CDRs of the murine antibody were cloned into a library containing all human germline gene FRs (Dall'Acqua et al., 2005). The libraries were screened for binding in a two-step selection process, first humanizing $V_L$, followed by $V_H$. In a later study, a one-step FR shuffling process was successfully used (Damschroder et al., 2007). Oligonucleotide sequences encoding all known human germline light chain (κ) frameworks are disclosed in Dall'Acqua et al., 2005, as Appendix A. Oligonucleotide sequences encoding all known human germline heavy chain frameworks are disclosed in Dall'Acqua et al., 2005, as Appendix B.

Humaneering

Humaneering allows for isolation of antibodies that are 91-96% homologous to human germline gene antibodies. The method is based on experimental identification of essential minimum specificity determinants (MSDs) and on sequential replacement of non-human fragments into libraries of human FRs and assessment of binding. It begins with regions of the CDR3 of non-human $V_H$ and $V_L$ chains and progressively replaces other regions of the non-human antibody into the human FRs, including the CDR1 and CDR2 of both $V_H$ and $V_L$.

The methods for humanizing antibodies explained above are preferred when generating humanized antibodies that specifically bind to the conformational epitopes described herein. Nevertheless, the present invention is not limited to the above-mentioned methods for humanizing antibodies.

Some of the aforementioned humanization methods can be performed without information about the FR sequences in the donor antibody, namely the "Fixed FR Method" (a variant of CDR-grafting), Superhumanization, Framework-shuffling, and Humaneering. Variations of the "fixed FR method" were successfully carried out by Qin et al., 2007 and Chang et al., 2007. In particular, Qin et al. constructed an antibody fragment comprising a human heavy chain variable region in which the three CDR regions were replaced by antigenic peptides, which were derived from the CDR sequences of a murine antibody. Chang et al. continued these experiments and constructed an scFv fragment, in which all CDRs from the $V_H$ part and CDR3 from the $V_L$ part were replaced by antigenic peptides, which were derived from the CDR sequences of a murine antibody.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, $F(ab')_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody" as used herein, is intended to refer to an antibody which is substantially free of other antibodies having different antigenic specificities (e.g., an isolated antibody that specifically binds to C5a is substantially free of antibodies that specifically bind antigens other than C5a). An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. In one embodiment of the invention, a combination of "isolated" monoclonal antibodies relates to antibodies having different specificities and being combined in a well defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E. N. and Gold L. (2000), Aptamers as therapeutic and diagnostic agents. J. Biotechnol. 74(1):5-13). The nucleic acid aptamer may be a DNA or RNA molecule. The aptamers may contain modifications, e.g. modified nucleotides such as 2'-fluorine-substituted pyrimidines.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from nonimmunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of nonnatural amino acids).

"Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. Regarding variants and derivatives of a polypeptide, it is not required that the variant or derivative exhibits such an activity to the same extent as the parent polypeptide. A variant is regarded as a variant within the context of the present application, if it exhibits the relevant activity to a degree of at least 10% of the activity of the parent polypeptide. Likewise, a derivative is regarded as a derivative within the context of the present application, if it exhibits the relevant biological activity to a degree of at least 10% of the activity of the parent polypeptide. The relevant "biological activity" in the context of the present invention is a binding activity to a conformational epitope of C5a formed by amino acid sequences $X_1X_2ETCEX_3RX_4$ (SEQ ID NO: 18) and $X_5X_6KX_7X_8X_9L$ (SEQ ID NO: 19), wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I. A particularly relevant "biological activity" in the context of the present invention is a binding activity to the conformational epitope of human C5a formed by the amino acid sequences according to SEQ ID NO: 2 and SEQ ID NO: 3. Preferably, the relevant "biological activity" in the context of the present invention is a binding activity to the conformational epitope of human C5a formed by the amino acid sequences DETCEQR (SEQ ID NO: 4) and KDM. Assays for determining binding activity are known to a person of ordinary skill in the art and include ELISAs such as the one described in the Examples section.

As used herein, a "patient" means any mammal or bird who may benefit from a treatment with the target-binding moiety described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

According to the American College of Chest Physicians and the Society of Critical Care Medicine (Bone R. C. et al. (1992). "Definitions for sepsis and organ failure and guidelines for the use of innovative therapies in sepsis. The ACCP/SCCM Consensus Conference Committee. American College of Chest Physicians/Society of Critical Care Medicine". Chest 101 (6): 1644-55), there are different levels of sepsis:

Systemic Inflammatory Response Syndrome (SIRS):

Defined by the presence of two or more of the following findings:

- Body temperature <36° C. (97° F.) or >38° C. (100° F.) (hypothermia or fever).
- Heart rate >100 beats per minute (tachycardia).
- Respiratory rate >20 breaths per minute or, on blood gas, a Pa $CO_2$ less than 32 mm Hg (4.3 kPa) (tachypnea or hypocapnia due to hyperventilation).
- White blood cell count <4,000 cells/$mm^3$ or >12,000 cells/$mm^3$ (<$4\times10^9$ or >$12\times10^9$ cells/L), or greater than 10% band forms (immature white blood cells). (leukopenia, leukocytosis, or bandemia).

Sepsis:

Defined as SIRS in response to a confirmed infectious process. Infection can be suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans Severe Sepsis:

Defined as sepsis with organ dysfunction, hypoperfusion, or hypotension.

Septic Shock:

Defined as sepsis with refractory arterial hypotension or hypoperfusion abnormalities in spite of adequate fluid resuscitation. Signs of systemic hypoperfusion may be either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid).

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

As used herein, "administering" includes in vivo administration, as well as administration directly to tissue ex vivo, such as vein grafts.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (Hu et al., Curr. Opin., Biotechnol. 8: 148, 1997); "Serum free Media" (K. Kitano, Biotechnol. 17:73, 1991); and "Suspension Culture of Mammalian Cells" (Birch et al. Bioprocess Technol. 19: 251, 1990).

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the present invention is directed to a binding moiety which binds to a conformational epitope formed by amino acid sequences $X_1X_2ETCEX_3RX_4$ (SEQ ID NO: 18) and $X_5X_6KX_7X_8X_9L$ (SEQ ID NO: 19) of C5a, wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I. In other words, a binding moiety according to the first aspect binds at the same time to at least one amino acid within the amino acid sequence according to SEQ ID NO: 18 and to at least one amino acid within the amino acid sequence according to SEQ ID NO: 19.

SEQ ID NO: 18 is a consensus sequence determined by comparing amino acids 30-38 of human C5a with the corresponding amino acid sequences in *Pan troglodytes, Macaca mulatta, Sus scrofa, Equus caballus, Bos Taurus, Mus musculus, Rattus norvegicus, Canis lupus*, and *Monodelphis domestica*. SEQ ID NO: 19 is a consensus sequence determined by comparing amino acids 66-72 of human C5a with the corresponding amino acid sequences in *Pan troglodytes, Macaca mulatta, Sus scrofa, Equus caballus, Bos Taurus, Mus musculus, Rattus norvegicus, Canis lupus*, and *Monodelphis domestica*.

In preferred embodiments of the first aspect, the binding moiety binds to at least one amino acid of the amino acid sequence $X_2ETCEX_3R$ (SEQ ID NO: 20), wherein $X_2$ and $X_3$ are defined as above. SEQ ID NO: 20 is a shorter version of the consensus sequence according to SEQ ID NO: 18 and corresponds to amino acids 31-37 of human C5a.

In preferred embodiments of the first aspect, the binding moiety binds to at least one amino acid of the amino acid sequence $X_6KX_7X_8X_9$ (SEQ ID NO: 21), preferably $KX_7X_8$, wherein $X_6$, $X_7$, $X_8$, and $X_9$ are defined as above. SEQ ID NO: 21 is a shorter version of the consensus sequence according to SEQ ID NO: 19 and corresponds to amino acids 67-71 of human C5a. $KX_7X_8$ is a shorter version of the consensus sequence according to SEQ ID NO: 21 and corresponds to amino acids 68-70 of human C5a.

In particularly preferred embodiments, the binding moiety binds at the same time to at least one amino acid within the amino acid sequence $X_2ETCEX_3R$ (SEQ ID NO: 20) and to at least one amino acid within the amino acid sequence $KX_7X_8$, wherein $X_2$, $X_3$, $X_7$, and $X_8$ are defined as above.

In preferred embodiments of the first aspect, the conformational epitope is formed by (a) amino acid sequences NDETCEQRA (SEQ ID NO: 2) and SHKDMQL (SEQ ID NO: 3) of C5a (sequences from *Homo sapiens* and *Pan troglodytes*); (b) amino acid sequences HDETCEQRA (SEQ ID NO: 22) and SHKDLQL (SEQ ID NO: 23) of C5a (sequences from *Macaca mulatta*); (c) amino acid sequences DDETCEERA (SEQ ID NO: 24) and SHKNIQL (SEQ ID NO: 25) of C5a (sequences from *Sus scrofa*); (d) amino acid sequences DLETCEQRA (SEQ ID NO: 26) and SHKHIQL (SEQ ID NO: 27) of C5a (sequences from *Equus caballus*); (e) amino acid sequences DDETCEQRA (SEQ ID NO: 28) and HHKNMQL (SEQ ID NO: 29) of C5a (sequences from *Bos taurus*); (f) amino acid sequences FYETCEERV (SEQ ID NO: 30) and PHKPVQL (SEQ ID NO: 31) of C5a (sequences from *Mus musculus*); (g) amino acid sequences KYETCEQRV (SEQ ID NO: 32) and HHKGMLL (SEQ ID NO: 33) of C5a (sequences from *Rattus norvegicus*); (h)

amino acid sequences YDETCEQRA (SEQ ID NO: 34) and SNKPLQL (SEQ ID NO: 35) of C5a (sequences from *Canis lupus*); or (i) amino acid sequences THETCEKRL (SEQ ID NO: 36) and NHKPVIL (SEQ ID NO: 37) of C5a (sequences from Monodelphis *domestica*).

In preferred embodiments of the first aspect, the binding moiety binds to at least one amino acid of an amino acid sequence selected from the group consisting of (a) DETCEQR (SEQ ID NO: 4); (b) DETCEER (SEQ ID NO: 38); (c) LETCEQR (SEQ ID NO: 39); (e) YETCEER (SEQ ID NO: 40); (f) YETCEQR (SEQ ID NO: 41); and (g) HETCEKR (SEQ ID NO: 42).

In preferred embodiments of the first aspect, the binding moiety binds to at least one amino acid of an amino acid sequence selected from the group consisting of (a) HKDMQ (SEQ ID NO: 5), preferably KDM; (b) HKDLQ (SEQ ID NO: 43), preferably KDL; (c) HKNIQ (SEQ ID NO: 44), preferably KNI; (d) HKHIQ (SEQ ID NO: 45), preferably KHI; (e) HKNMQ (SEQ ID NO: 46), preferably KNM; (f) HKPVQ (SEQ ID NO: 47), preferably KPV; (g) HKGML (SEQ ID NO: 48), preferably KGM; (h) NKPLQ (SEQ ID NO: 49), preferably KPL; and (i) HKPVI (SEQ ID NO: 50), preferably KPV.

In particularly preferred embodiments of the first aspect, the C5a is human C5a. Thus, it is preferred that the binding moiety binds to a conformational epitope formed by amino acids NDETCEQRA (SEQ ID NO: 2) and SHKDMQL (SEQ ID NO: 3) of human C5a. In other words, a binding moiety according to this preferred embodiment of the first aspect binds at the same time to at least one amino acid within the amino acid sequence according to SEQ ID NO: 2 and to at least one amino acid within the amino acid sequence according to SEQ ID NO: 3. SEQ ID NO: 2 corresponds to amino acids 30-38 of human C5a. SEQ ID NO: 3 corresponds to amino acids 66-72 of human C5a. The amino acid sequence of human C5a is depicted in SEQ ID NO: 1. In more preferred embodiments of the first aspect, the binding moiety binds to at least one of amino acids DETCEQR (SEQ ID NO: 4). SEQ ID NO: 4 corresponds to amino acids 31-37 of human C5a. In more preferred embodiments of the first aspect, the binding moiety binds to at least one of amino acids HKDMQ (SEQ ID NO: 5), more preferably to at least one of amino acids KDM. SEQ ID NO: 5 correspond to amino acids 67-71 of human C5a; the sequence KDM corresponds to amino acids 68-70 of human C5a. In particularly preferred embodiments, the binding moiety binds at the same time to at least one amino acid within the amino acid sequence DETCEQR (SEQ ID NO: 4) and to at least one amino acid within the amino acid sequence KDM.

In preferred embodiments of the first aspect, the two sequences forming the conformational epitope (e.g. sequence pairs according to SEQ ID NO: 18 and 19; SEQ ID NO: 2 and 3; SEQ ID NO: 22 and 23; SEQ ID NO: 24 and 25; SEQ ID NO: 26 and 27; SEQ ID NO: 28 and 29; SEQ ID NO: 30 and 31; SEQ ID NO: 32 and 33; SEQ ID NO: 34 and 35; SEQ ID NO: 36 and 37) are separated by 1-50 contiguous amino acids that do not participate in binding to the binding moiety of the invention. In the following, such amino acids that do not participate in binding to the binding moiety of the invention will be referred to as "non-binding amino acids". The two sequences forming the conformational epitope are preferably separated by 6-45 contiguous non-binding amino acids, more preferably by 12-40 contiguous non-binding amino acids, more preferably by 18-35 contiguous non-binding amino acids, more preferably by 24-30 contiguous non-binding amino acids, more preferably by 25-29 contiguous non-binding amino acids, even more preferably by 26-28 contiguous non-binding amino acids, and most preferably by 27 contiguous non-binding amino acids.

In preferred embodiments of the first aspect, the binding moiety has a binding constant to C5a, preferably human C5a, with a $K_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less.

In preferred embodiments of the first aspect, one binding moiety exhibits at least 75% blocking activity, preferably at least 80% blocking activity, more preferably at least 85% blocking activity, more preferably at least 90% blocking activity, more preferably at least 95% blocking activity for biological effects induced by one molecule C5a, preferably human C5a. These preferred blocking activities refer to those embodiments, wherein the binding moiety comprises a single paratope binding to C5a, preferably human C5a. In embodiments, wherein the binding moiety comprises two or more C5a-specific paratopes, said blocking activities of at least 75%, preferably at least 80%, more preferably at least 85%, etc. are achieved when one binding-moiety molecule is contacted with a number of C5a molecules equal to the number of C5a-specific paratopes present in the binding moiety. In other words, when the paratopes of a binding moiety of the first aspect and C5a are present in equimolar concentrations, the binding moiety according to the first aspect exhibits at least 75% blocking activity, preferably at least 80% blocking activity, more preferably at least 85% blocking activity, more preferably at least 90% blocking activity, and more preferably at least 95% blocking activity for biological effects induced by C5a. A preferred biological effect to be blocked is C5a-induced lysozyme release from human whole blood cells. Assays for determining this C5a-induced lysozyme release and its blocking are described in the examples section.

In preferred embodiments of the first aspect, the binding moiety does not inhibit CH50 activity in human plasma. Assays for determining CH50 activity are known to the skilled person and are described below in the examples section.

In preferred embodiments of the first aspect, the binding moiety does not exhibit a blocking activity on at least one C5b induced biological effect, preferably the binding moiety does not exhibit a blocking activity on any C5b induced biological effect.

In preferred embodiments of the first aspect, the binding moiety is capable of reducing *E. coli* induced IL-8 production in human whole blood. Assays for measuring IL-8 production in whole blood are known to the skilled person and will be described below in the examples section.

In preferred embodiments of the first aspect, the binding moiety is selected from: (a) antibodies or antigen-binding fragments thereof; (b) oligonucleotides; (c) antibody-like proteins; or (d) peptidomimetics.

In preferred embodiments of the first aspect, the binding moiety is an antibody or an antigen-binding fragment thereof, said antibody being selected from the group consisting of polyclonal antibodies, monoclonal antibodies, monovalent antibodies, bispecific antibodies, heteroconjugate antibodies, multispecific antibodies, deimmunized antibodies, chimeric antibodies, humanized (in particular CDR-grafted) antibodies, and human antibodies.

In preferred embodiments of the first aspect, the binding moiety is an antigen-binding fragment of an antibody, said fragment being selected from the group consisting of Fab fragments, Fab' fragments, $F(ab')_2$ fragments, Fd fragments, Fv fragments, disulfide-linked Fvs (dsFv), single domain antibodies (also known as nanobodies), and single chain Fv (scFv) antibodies.

In a particularly preferred embodiment of the first aspect, the binding moiety is an antibody or an antigen-binding fragment thereof comprising. (i) a heavy chain CDR3 sequence as set forth in SEQ ID NO: 6; or (ii) a heavy chain CDR3 sequence as set forth in SEQ ID NO: 7; wherein the heavy chain CDR3 sequence optionally comprises 1, 2 or 3 amino acid exchanges, preferably conservative amino acid exchanges, 1, 2, or 3 amino acid deletions and/or 1, 2, or 3 amino acid additions.

Preferably, the antibody or fragment thereof further comprises: (i) a light chain CDR3 sequence as set forth in SEQ ID NO: 8; or (ii) a light chain CDR3 sequence as set forth in SEQ ID NO: 9; wherein the light chain CDR3 sequence optionally comprises 1, 2 or 3 amino acid exchanges, preferably conservative amino acid exchanges, 1, 2, or 3 amino acid deletions and/or 1, 2, or 3 amino acid additions.

Preferably, the antibody or fragment further comprises at least one of the following sequences: (i) a heavy chain CDR2 sequence according to SEQ ID NO: 10; (ii) a heavy chain CDR2 sequence according to SEQ ID NO: 11; (iii) a light chain CDR2 sequence according to SEQ ID NO: 12; (iv) a light chain CDR2 sequence according to SEQ ID NO: 13; (v) a heavy chain CDR1 sequence according to SEQ ID NO: 14; (vi) a heavy chain CDR1 sequence according to SEQ ID NO: 15; (vii) a light chain CDR1 sequence according to SEQ ID NO: 16; or (viii) a light chain CDR1 sequence according to SEQ ID NO: 17; wherein the heavy chain CDR2 sequence optionally comprises 1, 2 or 3 amino acid exchanges, preferably conservative amino acid exchanges, 1, 2, or 3 amino acid deletions and/or 1, 2, or 3 amino acid additions; wherein the light chain CDR2 sequence optionally comprises 1, 2 or 3 amino acid exchanges, preferably conservative amino acid exchanges, 1, 2, or 3 amino acid deletions and/or 1, 2, or 3 amino acid additions; wherein the heavy chain CDR1 sequence optionally comprises 1, 2 or 3 amino acid exchanges, preferably conservative amino acid exchanges, 1, 2, or 3 amino acid deletions and/or 1, 2, or 3 amino acid additions; wherein the light chain CDR1 sequence optionally comprises 1, 2 or 3 amino acid exchanges, preferably conservative amino acid exchanges, 1, 2, or 3 amino acid deletions and/or 1, 2, or 3 amino acid additions. Preferably, the total number of these optional changes in each one of the amino acid sequences according to SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, and SEQ ID NO: 17, i.e. the total number of exchanges, deletions and additions in each sequence, is 1 or 2.

In some embodiments of the first aspect, the binding moiety is an oligonucleotide. In these embodiments, it is further preferred that the oligonucleotide is a nucleic acid aptamer, such as a DNA aptamer or RNA aptamer or a mixed aptamer comprising DNA and RNA nucleotides. In some embodiments, one or more nucleotides may be replaced by modified nucleotides such as 2'-fluorine-substituted pyrimidines. Nucleic acid aptamers may also be conjugated with fluorescent reporter molecules, affinity tags and/or macromolecules. For example, conjugating the aptamer to polyethylenglycol (PEG) or to a comparable macromolecule will increase the biological half-life of the aptamer.

In some embodiments of the first aspect, the binding moiety is an antibody-like protein, e.g. an antibody-like protein as exemplified above in the “Definitions” section.

In some embodiments of the first aspect, the binding moiety is a peptidomimetic. Peptidomimetics suitable for practicing the present invention are preferably based on antibody-like proteins as described above.

A preferred embodiment of the first aspect is directed to the binding moiety for the prevention and or treatment of various disease involving acute inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving chronic types of inflammation such as renal glomerular diseases such as glomerulonephritis and other entities of renal failure, rheumatoid arthritis and similar auto-immune diseases such as Bechterew’s disease, lupus-type diseases, inflammatory bowel disease, Crohn’s disease, tumor growth, or solid organ cancer.

In a second aspect the present invention is directed to an antibody or an antigen-binding fragment thereof comprising: (i) a heavy chain CDR3 sequence as set forth in SEQ ID NO: 6; or (ii) a heavy chain CDR3 sequence as set forth in SEQ ID NO: 7; wherein the heavy chain CDR3 sequence optionally comprises 1, 2 or 3 amino acid exchanges, preferably conservative amino acid exchanges, 1, 2, or 3 amino acid deletions and/or 1, 2, or 3 amino acid additions. Preferably, the total number of these optional changes in the amino acid sequence of SEQ ID NO: 6, i.e. the total number of exchanges, deletions and additions, is 1 or 2. Preferably, the total number of these optional changes in the amino acid sequence of SEQ ID NO: 7, i.e. the total number of exchanges, deletions and additions, is 1 or 2.

In preferred embodiments of the second aspect, the antibody or antigen-binding fragment thereof further comprises: (i) a light chain CDR3 sequence as set forth in SEQ ID NO: 8; or (ii) a light chain CDR3 sequence as set forth in SEQ ID NO: 9; wherein the light chain CDR3 sequence optionally comprises 1, 2 or 3 amino acid exchanges, preferably conservative amino acid exchanges, 1, 2, or 3 amino acid deletions and/or 1, 2, or 3 amino acid additions. Preferably, the total number of these optional changes in the amino acid sequence of SEQ ID NO: 8, i.e. the total number of exchanges, deletions and additions, is 1 or 2. Preferably, the total number of these optional changes in the amino acid sequence of SEQ ID NO: 9, i.e. the total number of exchanges, deletions and additions, is 1 or 2.

The second aspect of the present invention also refers to an antibody or an antigen-binding fragment thereof comprising: (i) a light chain CDR3 sequence as set forth in SEQ ID NO: 8; or (ii) a light chain CDR3 sequence as set forth in SEQ ID NO: 9; wherein the light chain CDR3 sequence optionally comprises 1, 2 or 3 amino acid exchanges, 1, 2, or 3 amino acid deletions and/or 1, 2, or 3 amino acid additions. Preferably, the total number of these optional changes in the amino acid sequence of SEQ ID NO: 8, i.e. the total number of exchanges, deletions and additions, is 1 or 2. Preferably, the total number of these optional changes in the amino acid sequence of SEQ ID NO: 9, i.e. the total number of exchanges, deletions and additions, is 1 or 2.

In preferred embodiments of the second aspect, the antibody or antigen-binding fragment thereof further comprises at least one of the following sequences: (i) a heavy chain CDR2 sequence according to SEQ ID NO: 10; (ii) a heavy chain CDR2 sequence according to SEQ ID NO: 11; (iii) a light chain CDR2 sequence according to SEQ ID NO: 12; (iv) a light chain CDR2 sequence according to SEQ ID NO: 13; (v) a heavy chain CDR1 sequence according to SEQ ID NO: 14; (vi) a heavy chain CDR1 sequence according to SEQ ID NO: 15; (vii) a light chain CDR1 sequence according to SEQ ID NO: 16; or (viii) a light chain CDR1 sequence according to SEQ ID NO: 17; wherein the heavy chain CDR2 sequence optionally comprises 1, 2 or 3 amino acid exchanges, preferably conservative amino acid exchanges, 1, 2, or 3 amino acid deletions and/or 1, 2, or 3 amino acid additions; wherein the light chain CDR2 sequence optionally comprises 1, 2 or 3 amino acid exchanges, preferably conservative amino acid exchanges, 1, 2, or 3 amino acid deletions and/or 1, 2, or 3 amino acid additions; wherein the heavy chain CDR1 sequence optionally comprises 1, 2 or 3 amino acid exchanges, preferably conservative amino acid exchanges, 1, 2, or 3 amino acid deletions and/or 1, 2, or 3 amino acid additions; wherein the light chain CDR1 sequence optionally comprises 1, 2 or 3 amino acid exchanges, preferably conservative amino acid exchanges, 1, 2, or 3 amino acid deletions and/or 1, 2, or 3 amino acid additions. Preferably, the total number of these optional changes in each one of the amino acid sequences according to SEQ ID NO: 10, SEQ ID NO: 11, SEQ ID NO: 13, SEQ ID NO: 14, SEQ ID NO: 15, SEQ ID NO: 16, and SEQ ID NO: 17, i.e. the total number of exchanges, deletions and additions in each sequence, is 1 or 2.

In preferred embodiments of the second aspect, the antibody is selected from the group consisting of polyclonal antibodies, monoclonal antibodies, monovalent antibodies, bispecific antibodies, heteroconjugate antibodies, multispecific antibodies, deimmunized antibodies, chimeric antibodies, humanized (in particular CDR-grafted) antibodies, and human antibodies.

In preferred embodiments of the second aspect, the antigen-binding fragment of an antibody is selected from the group consisting of Fab fragments, Fab' fragments, $F(ab')_2$ fragments, Fd fragments, Fv fragments, disulfide-linked Fvs (dsFv), single domain antibodies (also known as nanobodies), and single chain Fv (scFv) antibodies.

In preferred embodiments of the second aspect, the antibody or antigen-binding fragment thereof binds to a conformational epitope formed by amino acid sequences $X_1X_2ETCEX_3RX_4$ (SEQ ID NO: 18) and $X_5X_6KX_7X_8X_9L$ (SEQ ID NO: 19) of C5a, wherein $X_1$ is selected from the group consisting of N, H, D, F, K, Y, and T; $X_2$ is selected from the group consisting of D, L, Y, and H; $X_3$ is selected from the group consisting of Q, E, and K; $X_4$ is selected from the group consisting of A, V, and L; $X_5$ is selected from the group consisting of S, H, P, and N; $X_6$ is selected from the group consisting of H and N; $X_7$ is selected from the group consisting of D, N, H, P, and G; $X_8$ is selected from the group consisting of M, L, I, and V; and $X_9$ is selected from the group consisting of Q, L, and I. In other words, an antibody or antigen-binding fragment according to the second aspect binds at the same time to at least one amino acid within the amino acid sequence according to SEQ ID NO: 18 and to at least one amino acid within the amino acid sequence according to SEQ ID NO: 19. Preferably, the antibody or antigen-binding fragment thereof binds to at least one amino acid of the amino acid sequence $X_2ETCEX_3R$ (SEQ ID NO: 20), wherein $X_2$ and $X_3$ are defined as above. Preferably, the antibody or antigen-binding fragment thereof binds to at least one amino acid of the amino acid sequence $X_6KX_7X_8X_9$ (SEQ ID NO: 21), more preferably $KX_7X_8$, wherein $X_6$, $X_7$, $X_8$, and $X_9$ are defined as above. In particularly preferred embodiments, the antibody or antigen-binding fragment thereof binds at the same time to at least one amino acid within the amino acid sequence $X_2ETCEX_3R$ (SEQ ID NO: 20) and to at least one amino acid within the amino acid sequence $KX_7X_8$, wherein $X_2$, $X_3$, $X_7$, and $X_8$ are defined as above.

In preferred embodiments of the second aspect, the conformational epitope is formed by (a) amino acid sequences NDETCEQRA (SEQ ID NO: 2) and SHKDMQL (SEQ ID NO: 3) of C5a (sequences from *Homo sapiens* and *Pan troglodytes*); (b) amino acid sequences HDETCEQRA (SEQ ID NO: 22) and SHKDLQL (SEQ ID NO: 23) of C5a (sequences from *Macaca mulatta*); (c) amino acid sequences DDETCEERA (SEQ ID NO: 24) and SHKNIQL (SEQ ID NO: 25) of C5a (sequences from *Sus scrofa*); (d) amino acid sequences DLETCEQRA (SEQ ID NO: 26) and SHKHIQL (SEQ ID NO: 27) of C5a (sequences from *Equus caballus*); (e) amino acid sequences DDETCEQRA (SEQ ID NO: 28) and HHKNMQL (SEQ ID NO: 29) of C5a (sequences from *Bos taurus*); (f) amino acid sequences FYETCEERV (SEQ ID NO: 30) and PHKPVQL (SEQ ID NO: 31) of C5a (sequences from *Mus musculus*); (g) amino acid sequences KYETCEQRV (SEQ ID NO: 32) and HHKGMLL (SEQ ID NO: 33) of C5a (sequences from *Rattus norvegicus*); (h) amino acid sequences YDETCEQRA (SEQ ID NO: 34) and SNKPLQL (SEQ ID NO: 35) of C5a (sequences from *Canis lupus*); or (i) amino acid sequences THETCEKRL (SEQ ID NO: 36) and NHKPVIL (SEQ ID NO: 37) of C5a (sequences from Monodelphis *domestica*). In more preferred embodiments of the second aspect, the antibody or antigen-binding fragment thereof binds to at least one amino acid within an amino acid sequence selected from the group consisting of (a) DETCEQR (SEQ ID NO: 4); (b) DETCEER (SEQ ID NO: 38); (c) LETCEQR (SEQ ID NO: 39); (e) YETCEER (SEQ ID NO: 40); (f) YETCEQR (SEQ ID NO: 41); and (g) HETCEKR (SEQ ID NO: 42). In even more preferred embodiments of the first aspect, the antibody or antigen-binding fragment thereof binds to at least one amino acid within an amino acid sequence selected from the group consisting of (a) HKDMQ (SEQ ID NO: 5), preferably KDM; (b) HKDLQ (SEQ ID NO: 43), preferably KDL; (c) HKNIQ (SEQ ID NO: 44), preferably KNI; (d) HKHIQ (SEQ ID NO: 45), preferably KHI; (e) HKNMQ (SEQ ID NO: 46), preferably KNM; (f) HKPVQ (SEQ ID NO: 47), preferably KPV; (g) HKGML (SEQ ID NO: 48), preferably KGM; (h) NKPLQ (SEQ ID NO: 49), preferably KPL; and (i) HKPVI (SEQ ID NO: 50), preferably KPV.

In particularly preferred embodiments of the second aspect, the C5a is human C5a. Thus, it is preferred that the antibody or antigen-binding fragment thereof binds to a conformational epitope formed by amino acids NDETCEQRA (SEQ ID NO: 2) and SHKDMQL (SEQ ID NO: 3) of human C5a. In other words, an antibody or antigen-binding fragment thereof according to this preferred embodiment of the second aspect binds at the same time to at least one amino acid within the amino acid sequence according to SEQ ID NO: 2 and to at least one amino acid within the amino acid sequence according to SEQ ID NO: 3. In more preferred embodiments of the second aspect, the antibody or antigen-binding fragment thereof binds to at least one amino acid within the amino acid sequence DETCEQR (SEQ ID NO: 4). In more preferred embodiments of the second aspect, the antibody or antigen-binding fragment thereof binds to at least one amino acid within the amino acid sequence HKDMQ (SEQ ID NO: 5), more preferably to at least one amino acid within the amino acid sequence KDM. In particularly preferred embodiments, the antibody or antigen-binding fragment thereof binds at the same time to at least one amino acid within the amino acid sequence DETCEQR (SEQ ID NO: 4) and to at least one amino acid within the amino acid sequence KDM.

In preferred embodiments of the second aspect, the antibody or antigen-binding fragment thereof has a binding constant to C5a, preferably human C5a, with a $K_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less.

In preferred embodiments of the second aspect, one antibody or antigen-binding fragment thereof exhibits at least 75% blocking activity, preferably at least 80% blocking activity, more preferably at least 85% blocking activity, more preferably at least 90% blocking activity, more preferably at least 95% blocking activity for biological effects induced by one molecule C5a, preferably human C5a. These preferred blocking activities refer to those embodiments, wherein the antibody (or the antigen-binding fragment thereof) comprises a single paratope binding to C5a, preferably human C5a. In embodiments, wherein the antibody (or the antigen-binding fragment thereof) comprises two or more C5a-specific paratopes, said blocking activities of at least 75%, preferably at least 80%, more preferably at least 85%, etc. are achieved when one binding-moiety molecule is contacted with a number of C5a molecules equal to the number of C5a-specific paratopes present in the antibody (or the antigen-binding fragment thereof). For example, a typical anti-C5a antibody of the IgG-type comprises two paratopes capable of binding to C5a, whereas a typical anti-C5a antibody of the IgM-type comprises ten paratopes capable of binding to C5a. Thus, blocking activity of an antibody of the IgG-type should be determined by contacting said antibody with C5a in a molar ratio of 1:2. Blocking activity of an antibody of the IgM-type should be determined by contacting said antibody with C5a in a molar ratio of 1:10. When choosing these molar ratios, the paratopes within the antibody and C5a are present in equimolar concentrations. In other words, when the paratopes of an antibody (or antigen-binding fragment thereof) according to the second aspect and C5a are present in equimolar concentrations, the antibody or antigen-binding fragment thereof exhibits at least 75% blocking activity, preferably at least 80% blocking activity, more preferably at least 85% blocking activity, more preferably at least 90% blocking activity, and more preferably at least 95% blocking activity for biological effects induced by C5a. A preferred biological effect to be blocked is C5a-induced lysozyme release from human whole blood cells. Assays for determining this C5a-induced lysozyme release and its blocking are described in the examples section.

In preferred embodiments of the second aspect, the antibody or antigen-binding fragment thereof does not inhibit CH50 activity in human plasma. Assays for determining CH50 activity are known to the skilled person and are described below in the examples section.

In preferred embodiments of the second aspect, the antibody or antigen-binding fragment thereof does not exhibit a blocking activity on at least one C5b induced biological effect, preferably the antibody or antigen-binding fragment thereof does not exhibit a blocking activity on any C5b induced biological effect.

In preferred embodiments of the second aspect, the antibody or antigen-binding fragment thereof is capable of reducing *E. coli* induced IL-8 production in human whole blood. Assays for measuring IL-8 production in whole blood are known to the skilled person and will be described below in the examples section.

A preferred embodiment of the second aspect is directed to the antibody or antigen-binding fragment thereof for the prevention and or treatment of various diseases involving acute inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving chronic types of inflammation such as renal glomerular diseases such as glomerulonephritis and other entities of renal failure, rheumatoid arthritis and similar auto-immune diseases such as Bechterew's disease, lupus-type diseases, inflammatory bowel disease, Crohn's disease, tumor growth, or solid organ cancer.

In preferred embodiments of the first and the second aspect, the antibody or antigen-binding fragment thereof comprises one of the sets of heavy chain CDR3, heavy chain CDR2, and heavy chain CDR1 sequences as listed below in Table 1, wherein each heavy chain CDR3 sequence optionally comprises 1, 2 or 3 amino acid exchanges, preferably conservative amino acid exchanges, 1, 2, or 3 amino acid deletions and/or 1, 2, or 3 amino acid additions; wherein each heavy chain CDR2 sequence optionally comprises 1, 2 or 3 amino acid exchanges, preferably conservative amino acid exchanges, 1, 2, or 3 amino acid deletions and/or 1, 2, or 3 amino acid additions; and wherein each heavy chain CDR1 sequence optionally comprises 1, 2 or 3 amino acid exchanges, preferably conservative amino acid exchanges, 1, 2, or 3 amino acid deletions and/or 1, 2, or 3 amino acid additions:

TABLE 1

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| A | SEQ ID NO: 6 | SEQ ID NO: 10 | SEQ ID NO: 14 |
| B | SEQ ID NO: 6 | SEQ ID NO: 10 | SEQ ID NO: 15 |
| C | SEQ ID NO: 6 | SEQ ID NO: 11 | SEQ ID NO: 14 |
| D | SEQ ID NO: 6 | SEQ ID NO: 11 | SEQ ID NO: 15 |
| E | SEQ ID NO: 7 | SEQ ID NO: 10 | SEQ ID NO: 14 |
| F | SEQ ID NO: 7 | SEQ ID NO: 10 | SEQ ID NO: 15 |
| G | SEQ ID NO: 7 | SEQ ID NO: 11 | SEQ ID NO: 14 |
| H | SEQ ID NO: 7 | SEQ ID NO: 11 | SEQ ID NO: 15 |

In preferred embodiments of the first and the second aspect, the antibody or antigen-binding fragment thereof comprises one of the following sets of light chain CDR3, light chain CDR2, and light chain CDR1 sequences as listed in Table 2, wherein each light chain CDR3 sequence optionally comprises 1, 2 or 3 amino acid exchanges, preferably conservative amino acid exchanges, 1, 2, or 3 amino acid deletions and/or 1, 2, or 3 amino acid additions; wherein each light chain CDR2 sequence optionally comprises 1, 2 or 3 amino acid exchanges, preferably conservative amino acid exchanges, 1, 2, or 3 amino acid deletions and/or 1, 2, or 3 amino acid additions; and wherein each light chain CDR1 sequence optionally comprises 1, 2 or 3 amino acid exchanges, preferably conservative amino acid exchanges, 1, 2, or 3 amino acid deletions and/or 1, 2, or 3 amino acid additions:

Since the CDR2 light chain sequence of antibody INab308 (SEQ ID NO: 12) is identical to the CDR2 light chain sequence of antibody INab708 (SEQ ID NO: 13), sets including SEQ ID NO: 13 would be redundant to sets including SEQ ID NO: 12. Therefore, the table-Table 2 only list four sets of light chain CDR sequences.

TABLE 2

Sets of light chain CDR sequences suitable for use in the antibodies or fragments thereof of the present invention

| Number of light chain set | CDR3 sequence | CDR2 sequence | CDR1 sequence |
|---|---|---|---|
| I | SEQ ID NO: 8 | SEQ ID NO: 12 | SEQ ID NO: 16 |
| II | SEQ ID NO: 8 | SEQ ID NO: 12 | SEQ ID NO: 17 |
| III | SEQ ID NO: 9 | SEQ ID NO: 12 | SEQ ID NO: 16 |
| IV | SEQ ID NO: 9 | SEQ ID NO: 12 | SEQ ID NO: 17 |

In preferred embodiments of the first and the second aspect, the antibody or antigen-binding fragment thereof comprises one of the heavy CDR sets A-H listed above in Table 1 and one of the light chain CDR sets I-IV listed above in Table 2, i.e. one of the following combinations of sets: A-I, A-II, A-III, A-IV, B-I, B-II, B-III, B-IV, C-I, C-II, C-III, C-IV, D-I, D-II, D-III, D-IV, E-I, E-II, E-III, E-IV, F-I, F-II, F-III, F-IV, G-I, G-II, G-III, G-IV, H-I, H-II, H-III, or H-IV, wherein each heavy chain CDR3 sequence optionally comprises 1, 2 or 3 amino acid exchanges, preferably conservative amino acid exchanges, 1, 2, or 3 amino acid deletions and/or 1, 2, or 3 amino acid additions; wherein each heavy chain CDR2 sequence optionally comprises 1, 2 or 3 amino acid exchanges, preferably conservative amino acid exchanges, 1, 2, or 3 amino acid deletions and/or 1, 2, or 3 amino acid additions; wherein each heavy chain CDR1 sequence optionally comprises 1, 2 or 3 amino acid exchanges, preferably conservative amino acid exchanges, 1, 2, or 3 amino acid deletions and/or 1, 2, or 3 amino acid additions; wherein each light chain CDR3 sequence optionally comprises 1, 2 or 3 amino acid exchanges, preferably conservative amino acid exchanges, 1, 2, or 3 amino acid deletions and/or 1, 2, or 3 amino acid additions; wherein each light chain CDR2 sequence optionally comprises 1, 2 or 3 amino acid exchanges, preferably conservative amino acid exchanges, 1, 2, or 3 amino acid deletions and/or 1, 2, or 3 amino acid additions; and wherein each light chain CDR1 sequence optionally comprises 1, 2 or 3 amino acid exchanges, preferably conservative amino acid exchanges, 1, 2, or 3 amino acid deletions and/or 1, 2, or 3 amino acid additions.

In preferred embodiments of the first and the second aspect, the antibody or antigen-binding fragment thereof comprises a VH domain that comprises, essentially consists of or consists of (i) the VH domain of INab308 or (ii) the VH domain of INab708.

The FR1, CDR1, FR2, CDR2, FR3, CDR3, and FR4 sequences defining the VH domains of INab308 and INab708 are shown below in Table 4.

In preferred embodiments of the first and the second aspect, the antibody or antigen-binding fragment thereof comprises a VL domain that comprises, essentially consists of or consists of (i) the VL domain of INab308 or (ii) the VL domain of INab708.

The FR1, CDR1, FR2, CDR2, FR3, CDR3, and FR4 sequences defining the VL domains of INab308 and INab708 are shown below in Table 4.

In further preferred embodiments of the first and the second aspect, the antibody or antigen-binding fragment thereof comprises a VH domain and a VL domain, wherein (i) said VH domain comprises, essentially consists of or consists of the VH domain of INab308 and said VL domain comprises, essentially consists of or consists of the VL domain of INab308; or (i) said VH domain comprises, essentially consists of or consists of the VH domain of INab708 and said VL domain comprises, essentially consists of or consists of the VL domain of INab708.

In preferred embodiments of the first and the second aspect, the antibody or antigen-binding fragment thereof comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

The teaching given herein with respect to specific nucleic acid and amino acid sequences, e.g. those shown in the sequence listing, is to be construed so as to also relate to modifications of said specific sequences resulting in sequences which are functionally equivalent to said specific sequences, e.g. amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain effector functions of an antibody. Preferably, a sequence modified with respect to a specific sequence, when it replaces the specific sequence in an antibody retains binding of said antibody to C5a, in particular to the conformational epitope of C5a identified herein, and preferably retains functions of said antibody as described herein, e.g. blocking C5a-induced lysozyme release from human whole blood cells and/or reducing *E. coli* induced IL-8 production in human whole blood.

It will be appreciated by those skilled in the art that in particular the sequences of the CDR, hypervariable and variable regions can be modified without losing the ability to bind C5a. For example, CDR regions will be either identical or highly homologous to the regions specified herein. By "highly homologous" it is contemplated that from 1 to 5, preferably from 1 to 4, such as 1 to 3 or 1 or 2 substitutions, deletions, or additions may be made in the CDRs. In addition, the hypervariable and variable regions may be modified so that they show substantial homology with the regions specifically disclosed herein.

Furthermore, it may be desired according to the present invention to modify the amino acid sequences described herein, in particular those of human heavy chain constant regions to adapt the sequence to a desired allotype, e.g. an allotype found in the Caucasian population.

The present invention further comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260.

The in vivo half-life of antibodies can be improved by modifying the salvage receptor epitope of the Ig constant domain or an Ig-like constant domain such that the molecule does not comprise an intact CH2 domain or an intact Ig Fc region, cf. U.S. Pat. Nos. 6,121,022 and 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC of the antibodies in the presence of NK cells, cf. Shield et al. (2002) JBC, 277: 26733. Furthermore, modification of galactosylation can be made in order to modify CDC.

Alternatively, in another embodiment, mutations can be introduced randomly along all or part of an anti-C5a antibody coding sequence, such as by saturation mutagenesis, and the resulting modified anti-C5a antibodies can be screened for binding activity.

In a third aspect the present invention is directed to a pharmaceutical composition comprising (a) the binding moiety according to the first aspect or (b) the antibody or antigen-binding fragment thereof according to the second aspect, and further comprising one or more pharmaceutically acceptable carriers, diluents, excipients, fillers, binders, lubricants, glidants, disintegrants, adsorbents, and/or preservatives.

In a fourth aspect the present invention is directed to a use of (a) a binding moiety according to the first aspect or (b) an antibody or antigen-binding fragment thereof according to the second aspect, for the preparation of a pharmaceutical composition for the prevention and or treatment of various diseases involving acute inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving chronic types of inflammation such as renal glomerular diseases such as glomerulonephritis and other entities of renal failure, rheumatoid arthritis and similar auto-immune diseases such as Bechterew's disease, lupus-type diseases, inflammatory bowel disease, Crohn's disease, tumor growth, or solid organ cancer.

In a fifth aspect the present invention is directed to a method of preventing and or treating various diseases involving acute inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving chronic types of inflammation such as renal glomerular diseases such as glomerulonephritis and other entities of renal failure, rheumatoid arthritis and similar auto-immune diseases such as Bechterew's disease, lupus-type diseases, inflammatory bowel disease, Crohn's disease, tumor growth, or solid organ cancer in a patient in need thereof, the method comprising administering to the patient an effective amount of (a) a binding moiety according to the first aspect or (b) an antibody or antigen-binding fragment thereof according to the second aspect.

In the practice of any aspect of the present invention, a pharmaceutical composition as described above or a binding moiety (e.g. an antibody or antigen-binding fragment thereof) may be administered to a patient by any route established in the art which provides a sufficient level of the binding moiety in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated, e.g. into the organ afflicted by a tumour.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient: Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, an inhibitor of chemoattraction can be delivered in a controlled-release system. For example, the inhibitor may be administered using intravenous infusion, an implantable osmotic pump, a transdermal patch, liposomes, or other modes of administration. In one embodiment, a pump may be used (see Sefton (1987) *CRC Crit. RefBiomed. Eng.* 14: 201; Buchwald et al. (1980) *Surgery* 88:507; Saudek et al. (1989) *N. Eng. J. Med.* 321: 574). In another embodiment, the compound can be delivered in a vesicle, in particular a liposome (see Langer (1990) *Science* 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et al. (1985) *Science* 228:190; During et al. (1989) *Ann. Neurol.* 25: 351; Howard et al. (1989) *J. Neurosurg.* 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, *Science* 249: 1527-1533).

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and or treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

In the practice of any aspect of the present invention relating to the prevention and or treatment of tumor growth or solid organ cancer, the subject being administered the binding moiety or antibody of the invention is additionally treated with a chemotherapeutic agent, radiation, or an agent that modulates, e.g., enhances or inhibits, the expression or activity of an Fc receptor, e.g., an Fc-gamma receptor, such as a cytokine. Typical cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin, cisplatin, taxotere, 5-fluoruracil, methotrexate, gemzitabin and cyclophosphamide.

The following figures and examples are merely illustrative of the present invention and should not be construed to limit the scope of the invention as indicated by the appended claims in any way.

Potential amino acids in C5a molecules for constitution of antibody epitopes were mutated into alanine, and these C5a mutants were tested for their bioactivity to induce lysozyme releases from human whole blood cells. C5a site mutation resulting in more than 50% bioactivity loss in comparison to human C5a was considered as a critical site for C5a biological function. These sites are 24, 29, 31, 37, 68, and 69.

Figure 2:
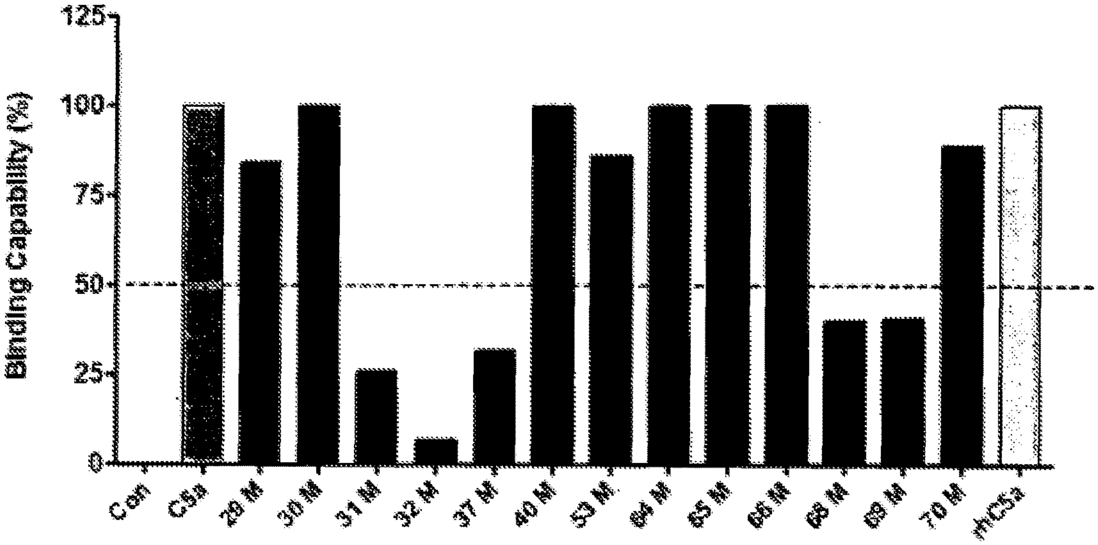

FIG. 2 Shows the Binding Capability of INab308 to C5a Mutants

C5a and C5a mutants were coated on a 96-well plate. The binding capabilities of INab308 to these proteins were assessed by ELISA approach. The loss of binding capability greater than 50% is considered significant. The data indicate that INab308 binds to two regions, 31-37 and 68-69.

Figure 3:
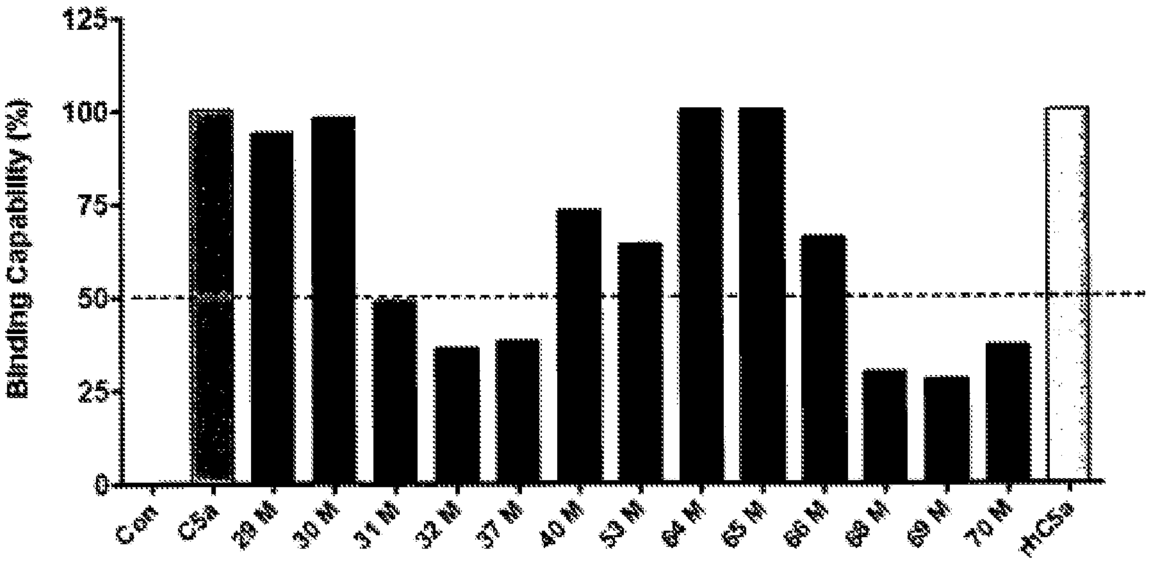

FIG. 3 Shows the Binding Capability of INab708 to C5a Mutants

C5a and C5a mutants were coated on a 96-well plate. The binding capabilities of INab708 to these proteins were assessed by ELISA approach. The loss of binding capability greater than 50% is considered significant. The data indicate that INab708 binds to two regions, 31-37 and 68-70.

Figure 4:
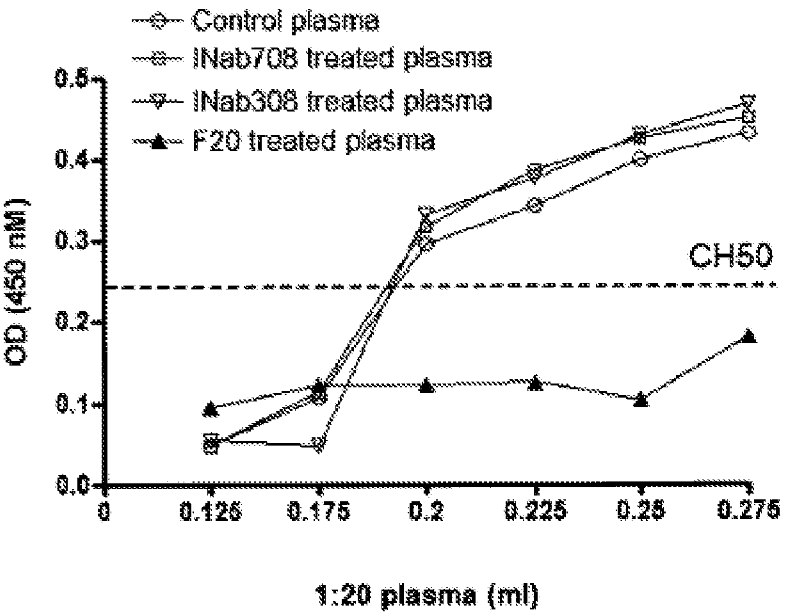

FIG. 4: INab308 and INab708 do not Affect Human Plasma CH50 Activity

Human plasma hemolytic activity was determined by classical CH50 assay. Mabs to human C5a including INab708, INab308, and F20, were pre-incubated with human plasma, and then CH50 assay was performed subsequently. Among these antibodies, F20 strongly inhibits CH50 activity, while INab708 and INab308 have no influence when used at a concentration of approx. 5 M, which is significantly higher than the C5 concentration occurring in human whole blood (approx. 0.4 μM).

Figure 5A:
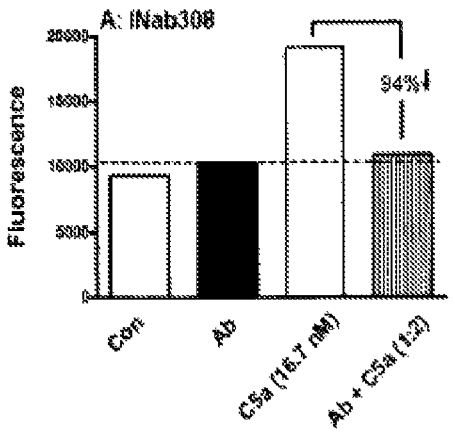
Figure 5B:
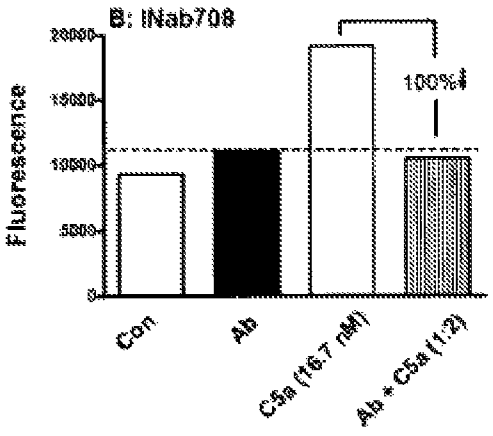
Figure 5C:
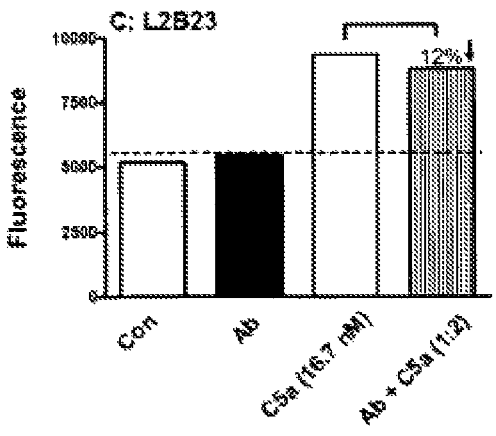

FIG. 5A-C Shows a Comparison of the Blocking Effects of INab308, INab708, and L2B23 on C5a Bioactivity Blocking activity of INab308, INab708 and L2B23 was assessed by C5a-induced lysozyme release assay. The molar ratio of antibody to C5a was set to 1:2 to evaluate the blocking activity of one antibody to two C5a molecules-elicited biological effect. The data show that INab308 and INab708 possess very high blocking activity (>90%) to C5a bioactivity, while L2B23 only shows a minimal effect.

Figure 6:
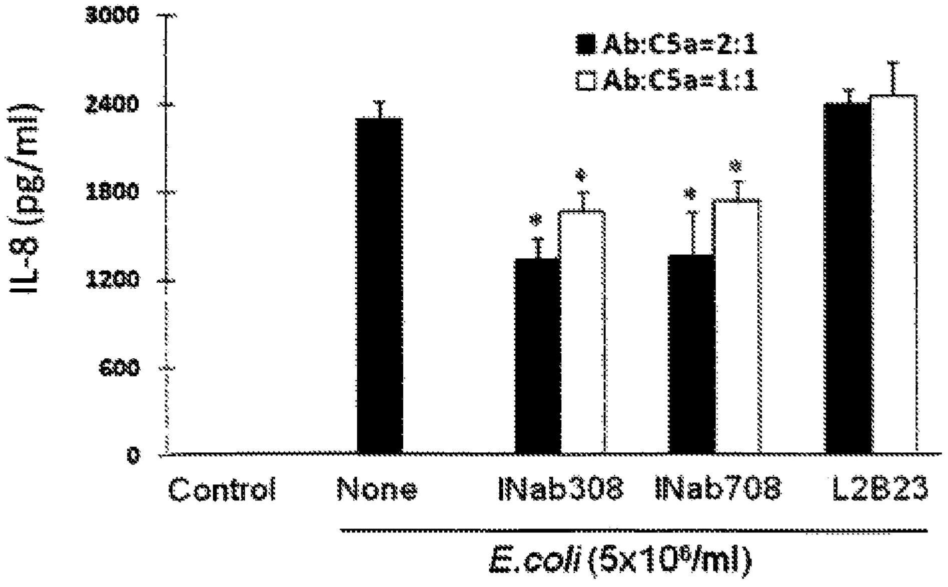

FIG. 6 Shows the Inhibitory Effect of INab308 and INab708 on *E. coli*-Induced IL-8 Production in Human Whole Blood

*E. coli* was incubated with whole blood for 4 hours, and IL-8 levels were assessed by ELISA. In the presence of INab308 and INab708 during the incubation, IL-8 levels were significantly attenuated (P<0.01), while there was no significant reduction in the presence of L2B23.

EXAMPLES

1. Methods 1.1 Recombinant C5a and C5a Mutant Preparation:

A DNA sequence encoding human C5a was obtained by reverse transcriptase-polymerase chain reaction (RT-PCR) using RNA isolated from peripheral blood leukocytes. C5a mutants were generated using PCR methods by introducing the GCT (alanine) into the mutation site. The C5a DNA was then ligated with pET-32a (NOVAGENIm, Gibbstown, N.J.), and the ligation mixture was used to transform JM109-competent cells. The expression plasmids were transformed into BL21 using a standard calcium chloride method. A single colony from a Luria-Bertani broth (LB) plate was picked up, inoculated into LB medium with ampicillin, and incubated at 37° C. overnight. The culture was transferred to 2 L of LB medium and incubated at 37° C. until the mid-exponential phase (A600≈0.6), and then isopropyl-β-D-thiogalactopyranoside (IPTG) was added to a final concentration of 0.1 mM. The cells were allowed to continue to grow at 30° C. overnight and harvested by spinning the culture at 7,000 rpm, 4° C., for 15 min. After washing with phosphate-buffered saline (PBS; 10 mM PB, 150 mM NaCl [pH 7.4]) once, the bacterial pellet was resuspended in PBS and sonicated on ice. After centrifugation at 12,000 rpm, 4° C., for 15 min, the soluble fraction was separated from insoluble pellet. To purify human recombinant C5a, the supernatant of cell lysate was loaded on a nickel-chelated affinity column preequilibrated with PBS. Then the column was washed with 50 mM imidazole and 200 mM imidazole in PBS, respectively. Finally, the bound proteins were eluted by 500 mM imidazole, dialyzed against PBS overnight, and analyzed by sodium dodecyl sulfate-polyacrylamide gel electrophoresis (SDS-PAGE).

1.2 Immunization and Hybridoma Screening by ELISA:

Monoclonal antibodies were made using hybridoma methods. Immunization and production of MAbs were carried out using standard protocols. Five 4-week-old female BALB/c mice were subcutaneously immunized with 100 μg of purified recombinant C5a in complete Freund's adjuvant per animal. The animals were boosted twice at 4-week intervals using 100 μg of antigen in incomplete Freund's adjuvant. Three days after the final booster, mice were sacrificed, and its splenocytes were fused with NS-1 at a 5:1 ratio, and 200 μL of cells was plated in each well on five 96-well plates. Hybrids were selected in a Dulbecco's Modified Eagle's Medium (DMEM) supplemented with 20% fetal calf serum and $5\times10^{-3}$ M hypoxanthine, $2\times10^{-5}$ M aminopterin, and $8\times10^{-4}$ M thymidine (HAT).

After 8 days, cell clones secreting antibodies against human C5a were screened by enzyme-linked immunosorbent assay (ELISA). Briefly, a 96-well plate was coated with 2 μg/mL recombinant human C5a at 4° C. overnight. After being blocked with 5% nonfat milk in PBS at 37° C. for 1 h, 50 μL of culture medium of the growing clones were added to each well and incubated at 37° C. for 1 h, followed by 100 μL of goat anti-mouse antibody labeled with horseradish peroxidase (HRP) for 1 h. The peroxidase reaction was developed with color development solution containing 5.5 mM o-phenylene-diamine hydrochloride (OPD) and 8.5 mM $H_2O_2$. The light absorbance was measured at 492 nm with an ELISA reader (ANTHOS™, Wals/Salzburg, Austria).

1.3 Production and Purification of Monoclonal Antibodies:

To produce the Mab in large quantity, $5\times10^{6}$ hybridoma cells were injected into the peritoneal cavity of mice. After 14 days, ascites were withdrawn and centrifuged at 1500 rpm, 4° C., for 5 min. The supernatant was collected and applied to a column of protein A-Sepharose 4B, which had been pre-equilibrated in PBS. The bound Mab was eluted with citric acid (pH 4.0) and dialyzed against PBS overnight. The purified proteins were analyzed by SDS-PAGE.

1.4 Enzyme Release Assay for C5a Bioactivity

Induction of enzyme releases by degranulation is an important biological feature of C5a. In our study, fresh human whole blood from healthy volunteers was used to assess the effect of C5a on lysozyme releases. The lysozyme levels released from whole blood cells were analyzed by EnzChek® Lysozyme Assay Kit (INVITROGEN™, CA, USA). To study the blocking activity of anti-05a antibodies, rhC5a (100 nM) was mixed with different concentration of antibody. Thereafter, whole blood cells were immediately added to avoid pre-incubation of antibodies with C5a. After incubation, 50 μl of the sample supernatants were added to 50 μl of diluted substrate solution. Plate was incubated at 37° C. for 30 min in the dark and read out thereafter with PERKINELMER™ 1420 multilabel Counter (Massachusetts, USA). Fluorescence intensity was measured with an excitation at 490 nm and an emission at 525 nm and zero standard value (blank) was subtracted from all samples. Blocking activity of the antibody was calculated after the subtraction of fluorescence intensity of rhC5a-independent lysozyme release (buffer control) from fluorescence intensity of rhC5a-induced lysozyme release. Blocking activity was calculated with the following formula, blocking activity=$C5a_{Fluorescence}-(C5a+Ab)_{Fluorescence}/C5a_{Fluorescence}-\text{Buffer Control}_{Fluorescence}$.

1.5 ELISA Analysis of INab308 and INab708 Binding Capability to Human C5a or C5a Mutants A binding Elisa was carried out to determine the binding activities of INab308 and INab708 to human C5a and C5a mutants. C5a mutants are produced by replacing the correspondent amino acid with alanine by introduction of GCT into the mutation site from the cDNA level. These C5a mutants include site mutation on 24, 29, 30, 31, 32, 35, 36, 37, 30/37 double mutation, 40, 53, 64, 65, 66, 68, 64/68, 66/68, 69, 70, and C-del (12 amino acids were deleted from C5a C terminus).

Human C5a (Sigma C5788), recombinant C5a, and C5a mutants (2 μg/mL) were coated on 96-well EIA plate (COSTAR™ 9018) at 4° C. overnight. After being blocked with 5% nonfat milk in PBS at 37° C. for 1 h, 0.08, 0.4, 2 μg/ml of anti-05a antibodies (INab308 and INab708) prepared with dilution buffer were added to each well and incubated at 37° C. for 1 h, followed by 100 μL of goat anti-mouse antibody labeled with horseradish peroxidase (HRP) for 1 h. The peroxidase reaction was developed with color development solution containing 5.5 mM o-phenylene-diamine hydrochloride (OPD) and 8.5 mM $H_2O_2$. The light absorbance was measured at 492 nm with an ELISA reader (ANTHOS™, Wals/Salzburg, Austria). The OD value for recombinant C5a was set as 100% binding activity. The binding capability of C5a mutants is calculated by $OD_{C5a\ mutant}/OD_{C5a}$.

1.6 Plasma Hemolytic Activity (CH50):

In brief, sheep red blood cells (sRBC) were prepared from fresh sheep whole blood by centrifugation, and then were sensitized with anti-sRBC. Plasma samples from healthy volunteers were serially diluted and incubated with sensitized sRBC. Half an hour after incubation, the unlysed cells were spun down, and the supernatants were read at 542 nm on a plate reader. To determine the effect of anti-C5a antibodies on C5 activation, equal volumes of anti-C5a antibody and plasma were pre-incubated for 1 hour prior to the addition of sensitized sRBC.

1.7 IL-8 Production in the Whole Blood Model of *E. coli* Infection:

To assess the efficacy of anti-C5a antibodies in the setting close to clinical sepsis, 250 μl of whole blood from healthy volunteers were spiked with anti-C5a antibodies, and 250 μl of *E. coli* diluted in saline buffer with a concentration of $1\times10^7$/ml were then added. After 4-hour incubation at 37° C., the supernatants were spun down and collected for ELISA analysis for IL-8. IL-8 levels in the supernatants were analyzed by IL-8 ELISA kit (BIOLEGEND™, USA).

1.8 Assay for Screening Antibodies Binding to the New Conformational Epitope:

In 3-D structure of C5a obtained from computer modeling method, the spatial epitopes containing peptide C5a 28-40 (VNNDETCEQRAAR, SEQ ID NO: 67) and C5a peptide 65-70 (ISHKDM, SEQ ID NO: 68) can be viewed as random coils. When the two peptides are linked by a flexible peptide linker, GGGGS (SEQ ID NO: 69), the spatial epitopes is reconstructed resembling the parent antigen conformation, as the weak hydrophobic interaction from the two peptides ensures a pocket-shape conformation. Computer modeling analysis of the peptide $NH_2$-28-40-Linker(GGGGS)-65-70-COOH maintains the same conformation as the parent antigen. This new 24-AA peptide can be synthesized and conjugated with keyhole limpet hemocyanin (KLH) to form an immunogen to immunize mice, and the traditional hybridoma technology can be subsequently applied to obtain INab308 and INab708 using the new 24-AA peptide based ELISA as a screening tool.

A 96-well ELISA plate is coated with 1-2 μg/mL synthetic peptides with the conformational epitope at 4° C. overnight. After being blocked with 5% nonfat milk in PBS at 37° C. for 1 h, 50 μL of culture media of the hybridoma growing clones are added to each well and incubated at 37° C. for 1 h, followed by 100 μL of goat anti-mouse antibody labeled with horseradish peroxidase (HRP) for 1 h. The peroxidase reaction is developed with color development solution containing 5.5 mM o-phenylene-diamine hydrochloride (OPD) and 8.5 mM $H_2O_2$. The light absorbance is measured at 492 nm with an ELISA reader.

2. Results 2.1 Identification of Amino Acids Relevant for C5a Activity

Figure 1:
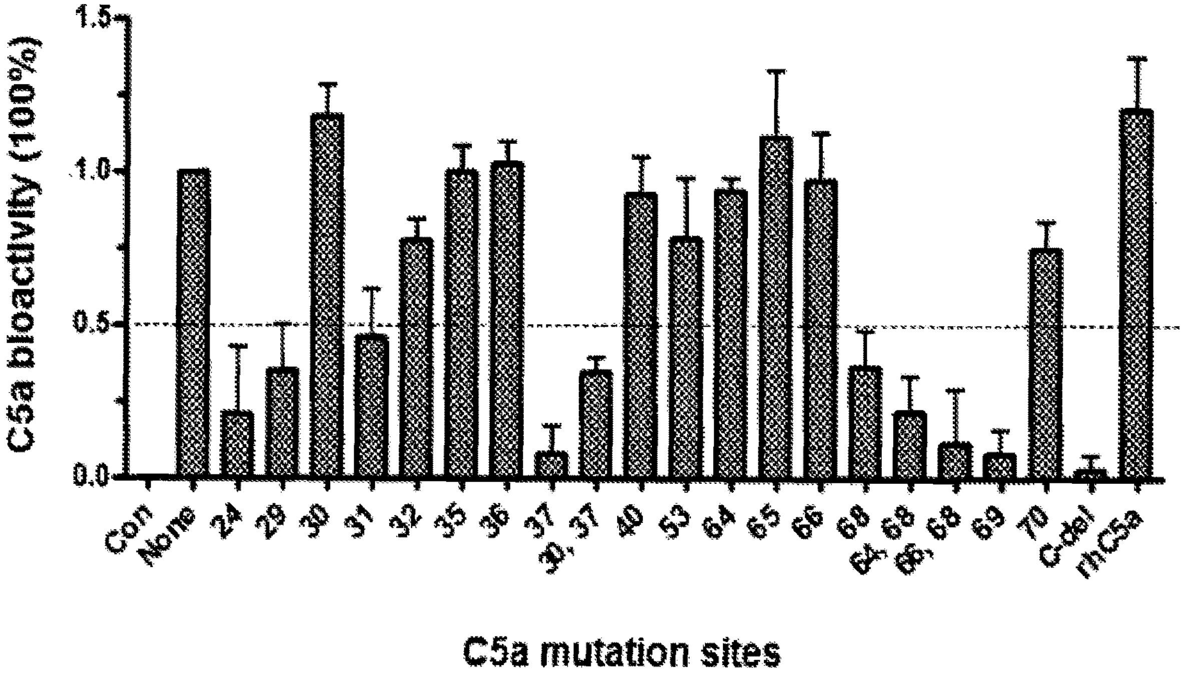
FIG. 1 Shows the Effect of C5a Mutants on Enzyme Releases from Blood Cells

Several amino acids within the C5a molecule that constitute possible antibody epitopes were mutated into alanine. In particular, C5a mutants include site mutations on 24, 29, 30, 31, 32, 35, 36, 37, 30/37 double mutation, 40, 53, 64, 65, 66, 68, 64/68, 66/68, 69, 70, and C-del (12 amino acids were deleted from the C-terminus of C5a). The C5a mutants were tested for their bioactivity to induce lysozyme release from human whole blood cells (FIG. 1).

C5a site mutation resulting in more than 50% bioactivity loss in comparison to human C5a was considered as a critical site for C5a biological function. Thus, amino acid residues 24, 29, 31, 37, 68, and 69 were identified as sites critical for function (FIG. 1).

2.2 Characterization of the Epitopes on C5a Bound by Antibodies INab308 and INab708

2000 cell clones secreting antibodies against human C5a were screened with the functional assay (enzyme release). Only two antibodies exhibited superior blocking activities.

These two antibodies, INab308 and INab708, were further characterized with respect to the particular amino acids on C5a recognized by the two antibodies.

In particular, several mutants of C5a were generated in which one or more amino acids were replaced by alanine. Antibodies INab308 and INab708 were contacted with these mutants and the extent of binding was determined by ELISA (see section 1.5 above). A loss of binding capability greater than 50% (as compared to wild-type C5a) was considered significant.

The data indicate that INab308 binds to two regions, 31-37 and 68-69 (FIG. 2). Likewise, INab708 binds to two regions, 31-37 and 68-70 (FIG. 3).

Notably, the regions identified for both antibodies cover four amino acid residues (31, 37, 68, and 69) that were identified as sites critical for C5a function in section 2.1 above.

2.3 Effect of Antibodies INab308, INab708, and F20 on Human Plasma Hemolytic Activity The total hemolytic complement titer (CH50) is a conventional method for determination of the activation of classical complement pathway (see section 1.6).

Monoclonal antibodies to C5a (INab708, INab308, and F20) were pre-incubated with human plasma at a concentration of approx. 5 μM, and then the CH50 assay was performed. Among these antibodies, F20 strongly inhibits CH50 activity, while INab708 and INab308 have no influence (FIG. 4).

These results demonstrate that INab708 and INab308 do not interfere with the complement activation mediated by C5b.

2.4 Effect of Antibodies INab308, INab708, and L2B23 on C5a Bioactivity

Blocking activity of antibodies INab308, INab708, and L2B23 on C5a was assessed by C5a-induced lysozyme release assay (see section 1.4). The molar ratio of antibody to C5a was set to 1:2 to evaluate the blocking activity of one antibody to two C5a molecules-elicited biological effect. These antibodies are bivalent antibodies. Accordingly, by choosing the above molar ratio of 1:2, the paratopes of the antibodies on the one hand and C5a on the other hand are present in equimolar concentrations.

The data in FIG. 5 show that INab308 and INab708 possess very high blocking activity to C5a bioactivity (94% and 100%, respectively), while L2B23 only shows a minimal effect (about 12%).

2.5 Effect of Antibodies INab308 and INab708 on *E. coli*-Induced IL-8 Production in Human Whole Blood To assess the efficacy of anti-C5a antibodies in a setting close to clinical sepsis, *E. coli*-induced IL-8 production in whole blood was determined. This assay can be regarded as a model of *E. coli* infection (see also section 1.7).

In the presence of INab308 and INab708 during the incubation, IL-8 levels were significantly attenuated (P<0.01), while there was no significant reduction in the presence of L2B23 (FIG. 6).

3. Summary

Important properties of preferred antibodies of the invention INab308 and INab708 are summarized in Table 3 below. Further included are comparative antibodies 8g8, MAb 137-26, Ab11876, G57, F20, L2B23, and G13 which do not bind simultaneously to both amino sequences of the conformational epitope identified in the present invention, i.e. amino acid sequences of SEQ ID NO: 2 and SEQ ID NO: 3. Comparative antibodies 8g8, MAb 137-26, F20, G57, L2B23, and G13 bind to only one of these two amino acid sequences (8g8, MAb 137-26, F20, G57, and G13) or to a different amino acid sequence (L2B23). The target epitope of Ab 11876 is not known.

Monoclonal antibodies to human C5a were generated using classical hybridoma technology. Mabs' binding sites to human C5a were determined by alanine screening method. Mabs' blocking activities were quantitated by inhibition of C5a-induced lysozyme releases from human whole blood cells.

TABLE 3

Neutralizing antibodies to C5a and the epitopes

| Antibody | Binding sites | Affinity (Kd: nM) | Ratio of Ab to C5a | Blocking activity |
|---|---|---|---|---|
| INab308 | 31-37, 68-69 | 0.50 | 1/2:1 | ≥90% |
| INab708 | 31-37, 68-70 | 0.51 | 1/2:1 | ≥90% |
| 8g8 | 69-74 | 0.27 | 1/2:1 | 60% |
| MAb 137-26* | 35-46 | 0.06 | 1/2:1 | 55% |
| Ab11876** | ND | ND | 4:1 | 40% |
| G57 | 31-37 | ND | 4:1 | 40% |
| F20 | 68-69 | 7.06 | 10:1 | 70% |
| L2B23 | 64-66 | ND | 10:1 | 50% |
| G13 | 53, 66-68 | ND | 10:1 | 60% |

ND: Not determined;

*ATCC clone no. PTA-3650 relating to an antibody disclosed in European patent application 1 878 441 A2;

**Ab11876 is a monoclonal mouse anti C5/C5a antibody obtainable from ABCAM (Cambridge, UK).

As shown in Table 3, some comparative antibodies (8g8, MAb 137-26) exhibit higher binding affinities to C5a than the preferred antibodies of the invention, INab308 and INab708. Nevertheless, INab308 and INab708 exhibit higher blocking activities than any comparative antibody studied. More specifically, each one of INab308 and INab708 exhibits a very high blocking activity (>90%), even when used in stoichiometric amounts, i.e. at a ratio of 1 paratope per 1 epitope; i.e. 0.5 antibody molecules per 1 target molecule. Antibodies of the prior art (MAb 137-26, Ab11876) achieved reasonable blocking activities only when used in superstoichiometric amounts. These findings demonstrate that high binding affinity cannot always be equated with high blocking activity.

Summarizing, the present invention provides for the first time antibodies that exhibit an extremely high blocking activity, even when used just in stoichiometric amounts.

The amino acid sequences of the complementarity determining regions of the heavy and light chains of antibodies INab308 and INab708 are listed below in Table 4.

TABLE 4

CDR and FR sequences of antibodies INab308 and INab708 (*Chothia* classification mode)

| INab308: | INab708: |
|---|---|
| Heavy Chain: | Heavy Chain: |
| FR1:<br>QVQLQQSGPQLVRPGTSVKIS<br>(= SEQ ID NO: 51) | FR1:<br>VQLLESGAELMKPGASVKIS<br>(SEQ ID NO: 59) |
| CDR1:<br>CKASGYSFTTFWMD<br>(= SEQ ID NO: 14) | CDR1:<br>CKATGNTFSGYWIE<br>(= SEQ ID NO: 15) |
| FR2:<br>WVKQRPGQGLEWIGR<br>(SEQ ID NO: 52) | FR2:<br>WVKQRPGHGLEWIGE<br>(SEQ ID NO: 60) |

TABLE 4-continued

CDR and FR sequences of antibodies INab308 and INab708 (*Chothia* classification mode)

| INab308: | INab708: |
|---|---|
| CDR2:<br>IDPSDSESRLDQ<br>(= SEQ ID NO: 10) | CDR2:<br>ILPGSGSTNYNE<br>(= SEQ ID NO: 11) |
| FR3:<br>RFKDRATLTVDKSSSTVYMQLSSPTSEDSAVYY<br>(SEQ ID NO: 53) | FR3:<br>KFKGKATLTADTSSNTAYMQLSSLTSEDSAVYY<br>(SEQ ID NO: 61) |
| CDR3:<br>CARGNDGYYGFAY<br>(= SEQ ID NO: 6) | CDR3:<br>CTRRGLYDGSSYFAY<br>(= SEQ ID NO: 7) |
| FR4:<br>WGQGTLVTVSSA<br>(SEQ ID NO: 54) | FR4:<br>WGQGTLVTVSA<br>(SEQ ID NO: 62) |
| Light chain: | Light Chain: |
| FR1:<br>DIVLTQSPASLAVSLGQRATIS<br>(SEQ ID NO: 55) | FR1:<br>DIVLTQSPASLAVSLGQRATIS<br>(SEQ ID NO: 63) |
| CDR1:<br>CKASQSVDYDGDSYMK<br>(= SEQ ID NO: 16) | CDR1:<br>CKASQSVDYDGDSYMN<br>(= SEQ ID NO: 17) |
| FR2:<br>WYQQKPGQPPKLL<br>(SEQ ID NO: 56) | FR2:<br>WYQQKPGQPPKLL<br>(SEQ ID NO: 64) |
| CDR2:<br>IYAASNL<br>(= SEQ ID NO: 12) | CDR2:<br>IYAASNL<br>(= SEQ ID NO: 13) |
| FR3:<br>QSGIPARFSGSGSGTDFTLNIHPVEEEDAATYY<br>(SEQ ID NO: 57) | FR3:<br>GSGIPARFSGSGSGTDFTLNIHPVEEEVAATYY<br>(SEQ ID NO: 65) |
| CDR3:<br>CQQSNEDPYT<br>(= SEQ ID NO: 8) | CDR3:<br>CQQNNEDPLT<br>(= SEQ ID NO: 9) |
| FR4:<br>FGGGTKLEIK<br>(SEQ ID NO: 58) | FR4:<br>FGAGTLLELK<br>(SEQ ID NO: 66) |

REFERENCES

Allegretti M, Moriconi A, Beccari A R, Di Bitondo R, Bizzarri C, Bertini R, and Colotta F. 2005. Targeting C5a: recent advances in drug discovery. Curr Med Chem 12(2):217-236.

Bengtson A, and Heideman M. 1988. Anaphylatoxin formation in sepsis. Arch Surg 123(5):645-649.

Czermak B J, Sarma V, Pierson C L, Warner R L, Huber-Lang M, Bless N M, Schmal H, Friedl H P, and Ward P A. 1999. Protective effects of C5a blockade in sepsis. Nat Med 5(7):788-792.

Guo R F, Huber-Lang M, Wang X, Sarma V, Padgaonkar V A, Craig R A, Riedemann N C, McClintock S D, Hlaing T, Shi M M and others. 2000. Protective effects of anti-C5a in sepsis-induced thymocyte apoptosis. J Clin Invest 106(10):1271-1280.

Guo R F, Riedemann N C, Laudes I J, Sarma V J, Kunkel R G, Dilley K A, Paulauskis J D, and Ward P A. 2002. Altered neutrophil trafficking during sepsis. J Immunol 169(1):307-314.

Guo R F, Riedemann N C, Sun L, Gao H, Shi K X, Reuben J S, Sarma V J, Zetoune F S, and Ward P A. 2006a. Divergent signaling pathways in phagocytic cells during sepsis. J Immunol 177(2):1306-1313.

Guo R F, Sun L, Gao H, Shi K X, Rittirsch D, Sarma V J, Zetoune F S, and Ward P A. 2006b. In vivo regulation of neutrophil apoptosis by C5a during sepsis. J Leukoc Biol 80(6):1575-1583.

Guo R F, and Ward P A. 2005. Role of C5a in inflammatory responses. Annu Rev Immunol 23:821-852.

Hopken U, Mohr M, Struber A, Montz H, Burchardi H, Gotze 0, and Oppermann M. 1996. Inhibition of interleukin-6 synthesis in an animal model of septic shock by anti-C5a monoclonal antibodies. Eur J Immunol 26(5): 1103-1109.

Huber-Lang M, Sarma V J, Lu K T, McGuire S R, Padgaonkar V A, Guo R F, Younkin E M, Kunkel R G, Ding J, Erickson R and others. 2001a. Role of C5a in multiorgan failure during sepsis. J Immunol 166(2):1193-1199.

Huber-Lang M S, Sarma J V, McGuire S R, Lu K T, Guo R F, Padgaonkar V A, Younkin E M, Laudes I J, Riedemann N C, Younger J G and others. 2001b. Protective effects of anti-C5a peptide antibodies in experimental sepsis. FASEB J 15(3):568-570.

Huber-Lang M S, Younkin E M, Sarma J V, McGuire S R, Lu K T, Guo R F, Padgaonkar V A, Curnutte J T, Erickson R, and Ward P A. 2002. Complement-induced impairment of innate immunity during sepsis. J Immunol 169(6): 3223-3231.

Klos A, Tenner A J, Johswich K O, Ager R R, Reis E S, and Kohl J. 2009. The role of the anaphylatoxins in health and disease. Mol Immunol 46(14):2753-2766.

Laudes I J, Chu J C, Sikranth S, Huber-Lang M, Guo R F, Riedemann N, Sarma J V, Schmaier A H, and Ward P A. 2002. Anti-c5a ameliorates coagulation/fibrinolytic protein changes in a rat model of sepsis. Am J Pathol 160(5):1867-1875.

Markiewski M M, DeAngelis R A, Benencia F, Ricklin-Lichtsteiner S K, Koutoulaki A, Gerard C, Coukos G, and Lambris J D. 2008. Modulation of the antitumor immune response by complement. Nat Immunol 9(11):1225-1235.

Nakae H, Endo S, Inada K, Takakuwa T, Kasai T, and Yoshida M. 1994. Serum complement levels and severity of sepsis. Res Commun Chem Pathol Pharmacol 84(2): 189-195.

Nakae H, Endo S, Inada K, and Yoshida M. 1996. Chronological changes in the complement system in sepsis. Surg Today 26(4):225-229.

Riedemann N C, Guo R F, Bernacki K D, Reuben J S, Laudes I J, Neff T A, Gao H, Speyer C, Sarma V J, Zetoune F S and others. 2003. Regulation by C5a of neutrophil activation during sepsis. Immunity 19(2):193-202.

Riedemann N C, Guo R F, Gao H, Sun L, Hoesel M, Hollmann T J, Wetsel R A, Zetoune F S, and Ward P A. 2004a. Regulatory role of C5a on macrophage migration inhibitory factor release from neutrophils. J Immunol 173(2):1355-1359.

Riedemann N C, Guo R F, Hollmann T J, Gao H, Neff T A, Reuben J S, Speyer C L, Sarma J V, Wetsel R A, Zetoune F S and others. 2004b. Regulatory role of C5a in LPS-induced IL-6 production by neutrophils during sepsis. FASEB J 18(2):370-372.

Riedemann N C, Guo R F, Neff T A, Laudes I J, Keller K A, Sarma V J, Markiewski M M, Mastellos D, Strey C W, Pierson C L and others. 2002a. Increased C5a receptor expression in sepsis. J Clin Invest 110(1):101-108.

Riedemann N C, Guo R F, Sarma V J, Laudes I J, Huber-Lang M, Warner R L, Albrecht E A, Speyer C L, and Ward P A. 2002b. Expression and function of the C5a receptor in rat alveolar epithelial cells. J Immunol 168(4):1919-1925.

Rittirsch D, Flierl M A, and Ward P A. 2008. Harmful molecular mechanisms in sepsis. Nat Rev Immunol 8(10): 776-787.

Strieter R M, Kasahara K, Allen R M, Standiford T J, Rolfe M W, Becker F S, Chensue S W, and Kunkel S L. 1992. Cytokine-induced neutrophil-derived interleukin-8. Am J Pathol 141(2):397-407.

Ward P A. 2009. Functions of C5a receptors. J Mol Med 87(4):375-378.

Almagro J C and Fransson J. 2008. Humanization of antibodies. Frontiers in Bioscience 13:1619-1633.

Chang H, Qin W, Li Y, Zhang J, Lin Z, Lv M, Sun Y, Feng J, and Shen B. 2007. A novel human scFv fragment against TNF-α from de novo design method. Molecular Immunology 44:3789-3796.

Dall'Acqua W F, Damschroder M M, Zhang J, Woods R M, Widjaja L, Yu J, and Wu H. 2005. Antibody humanization by framework shuffling. Methods 36:43-60.

Damschroder M M, Widjaja L, Gill P S, Krasnoperov V, Jiang W, Dall'Acqua W F, and Wu H. 2007. Framework shuffling of antibodies to reduce immunogenicity and manipulate functional and biophysical properties. Molecular Immunology 44:3049-3060.

Heap C J, Wang Y, Pinheiro T J T, Reading S A, Jennings K R, and Dimmock N J. 2005. Analysis of a 17-amino acid residue, virus-neutralizing microantibody. J. Gen. Virol. 86:1791-1800.

Qin W, Feng J, Li Y, Lin Z, and Shen B. 2007. A novel domain antibody rationally designed against TNF-α using variable region of human heavy chain as scaffolds to display antagonistic peptides. Molecular Immunology 44:2355-2361.

Qiu X-Q, Wang H, Cai B, Wang L-L, and Yue S-T. 2007. Small antibody mimetics comprising two complementary-determining regions and a framework region for tumor targeting. Nature biotechnology 25(8):921-929.

SEQUENCE LISTING FREE TEXT INFORMATION

SEQ ID NO: 6 INab308 CDR3 heavy chain
SEQ ID NO: 7 INab708 CDR3 heavy chain
SEQ ID NO: 8 INab308 CDR3 light chain
SEQ ID NO: 9 INab708 CDR3 light chain
SEQ ID NO: 10 INab308 CDR2 heavy chain
SEQ ID NO: 11 INab708 CDR2 heavy chain
SEQ ID NO: 12 INab308 CDR2 light chain
SEQ ID NO: 13 INab708 CDR2 light chain
SEQ ID NO: 14 INab308 CDR1 heavy chain
SEQ ID NO: 15 INab708 CDR1 heavy chain
SEQ ID NO: 16 INab308 CDR1 light chain
SEQ ID NO: 17 INab708 CDR1 light chain
SEQ ID NO: 18 Consensus sequence of C5a in the region of amino acids 30-38
SEQ ID NO: 19 Consensus sequence of C5a in the region of amino acids 66-72
SEQ ID NO: 20 Consensus sequence of C5a in the region of amino acids 31-37
SEQ ID NO: 21 Consensus sequence of C5 in the region of amino acids 67-71
SEQ ID NO: 51 INab308 FR1 heavy chain
SEQ ID NO: 52 INab308 FR2 heavy chain
SEQ ID NO: 53 INab308 FR3 heavy chain
SEQ ID NO: 54 INab308 FR4 heavy chain
SEQ ID NO: 55 INab308 FR1 light chain
SEQ ID NO: 56 INab308 FR2 light chain
SEQ ID NO: 57 INab308 FR3 light chain
SEQ ID NO: 58 INab308 FR4 light chain
SEQ ID NO: 59 INab708 FR1 heavy chain
SEQ ID NO: 60 INab708 FR2 heavy chain
SEQ ID NO: 61 INab708 FR3 heavy chain
SEQ ID NO: 62 INab708 FR4 heavy chain
SEQ ID NO: 63 INab708 FR1 light chain
SEQ ID NO: 64 INab708 FR2 light chain
SEQ ID NO: 65 INab708 FR3 light chain
SEQ ID NO: 66 INab708 FR4 light chain
SEQ ID NO: 69 Peptide linker

We claim:

1. An antibody or an antigen-binding fragment thereof comprising a VL and a VH domain, wherein the VL domain comprises a light chain CDR3 sequence having SEQ ID NO: 8, two tyrosine residues preceeding SEQ ID NO: 8 and a light chain FR4 comprising the sequence of SEQ ID NO: 58 or conservative amino acid substitution variants of SEQ ID NO: 58, wherein said antibody or said antigen-binding fragment thereof specifically binds to human C5a; and wherein said antibody or antigen-binding fragment thereof has a binding constant to human C5a with a $K_d$ value of 100 nM or less.

2. The antibody or the antigen-binding fragment thereof according to claim 1, wherein said antibody or said antigen-binding fragment thereof exhibits one or more of the following properties:

said antibody or said antigen-binding fragment thereof has a binding constant to C5a with a $K_d$ value of 10 nM or less;

said antibody or said antigen-binding fragment thereof exhibits at least 80% blocking activity for biological effects induced by one molecule C5a, wherein said biological effects are mediated by C5a-05aR interaction;

said antibody or said antigen-binding fragment thereof does not inhibit CH50 activity in human plasma; and said antibody or said antigen-binding fragment thereof is capable of reducing *E. coli* induced IL-8 production in human whole blood.

3. The antibody or the antigen-binding fragment thereof according to claim 1, wherein said antibody or said antigen-binding fragment is an antibody selected from the group consisting of polyclonal antibodies, monoclonal antibodies, chimeric antibodies, humanized antibodies, and human antibodies.

4. The antibody or the antigen-binding fragment thereof according to claim 1, wherein said antibody or said antigen-binding fragment is an antigen-binding fragment of an antibody selected from the group consisting of Fab fragments, Fab' fragments, $F(ab')_2$ fragments, Fv fragments, disulfide-linked Fvs (dsFv), and single chain Fv (scFv) antibodies.

5. A pharmaceutical composition comprising the antibody or antigen-binding fragment thereof according to claim 1 and further comprising one or more pharmaceutically acceptable carriers, diluents, excipients, fillers, binders, lubricants, glidants, disintegrants, adsorbents, and/or preservatives.

6. A method of blocking C5a-induced biological effects in a patient with acute or chronic inflammation, wherein said method comprises administering to a patient in need of such blocking of C5a-induced biological effects, the pharmaceutical composition of claim 5.

7. A method for the treatment of a disease involving acute or chronic inflammation, wherein said method comprises administering, to a patient in need of such treatment, the pharmaceutical composition of claim 5.

8. The method of claim 7, wherein the disease involving acute or chronic inflammation is selected from the group consisting of systemic inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer.

9. The antibody or the antigen-binding fragment thereof according to claim 1, wherein the conservative amino acid substitution variants of SEQ ID NO: 58 are hydrophobic amino acid substitutions.

10. The antibody or the antigen-binding fragment thereof according to claim 9, wherein at least one hydrophobic amino acid substitution is a leucine to valine substitution.

* * * * *